(12) United States Patent
Hyman et al.

(10) Patent No.: US 12,059,181 B2
(45) Date of Patent: Aug. 13, 2024

(54) SPINAL STABILITY SYSTEM

(71) Applicants: Eric Hyman, Wakefield, MA (US);
Vincent Lambert, Salisbury, MA (US);
Steven Lepke, Wakefield, MA (US);
Annika Linnea Shade Evensen,
Revere, MA (US)

(72) Inventors: Eric Hyman, Wakefield, MA (US);
Vincent Lambert, Salisbury, MA (US);
Steven Lepke, Wakefield, MA (US);
Annika Linnea Shade Evensen,
Revere, MA (US)

( * ) Notice: Subject to any disclaimer, the term of this patent is extended or adjusted under 35 U.S.C. 154(b) by 0 days.

(21) Appl. No.: 18/514,825

(22) Filed: Nov. 20, 2023

(65) Prior Publication Data

US 2024/0206924 A1 Jun. 27, 2024

Related U.S. Application Data

(63) Continuation-in-part of application No. 18/497,922, filed on Oct. 30, 2023, which is a continuation of application No. 18/087,738, filed on Dec. 22, 2022, now Pat. No. 11,839,414.

(51) Int. Cl.
*A61B 17/70* (2006.01)

(52) U.S. Cl.
CPC ...... *A61B 17/7085* (2013.01); *A61B 17/7097* (2013.01)

(58) Field of Classification Search
CPC .............. A61B 17/7085; A61B 17/7097
USPC .............. 606/246–279; 623/17.11–17.16
See application file for complete search history.

(56) References Cited

U.S. PATENT DOCUMENTS

| | | | |
|---|---|---|---|
| 10,172,656 B1 * | 1/2019 | Reimels | A61B 17/8625 |
| 2007/0173939 A1 * | 7/2007 | Kim | A61B 17/8858 |
| | | | 623/17.11 |
| 2011/0319946 A1 * | 12/2011 | Levy | A61B 17/8685 |
| | | | 606/300 |

* cited by examiner

*Primary Examiner* — Eduardo C Robert
*Assistant Examiner* — Tara Rose E Carter
(74) *Attorney, Agent, or Firm* — Jones Day

(57) ABSTRACT

A device for a spinal stabilization procedure includes a cannulated tubular body configured to be inserted into a spinal surgical site and an expansion component coupled to the cannulated tubular body. The expansion component can include a plurality of elongated mechanical supports which can be axially aligned with the cannulated tubular body when in a collapsed state, and which can bend outward in a radial direction when in an expanded state. The mechanical expansion can be controlled using one or more adjustment elements of the device. Related apparatus, systems, kits, techniques and articles are also described.

22 Claims, 28 Drawing Sheets

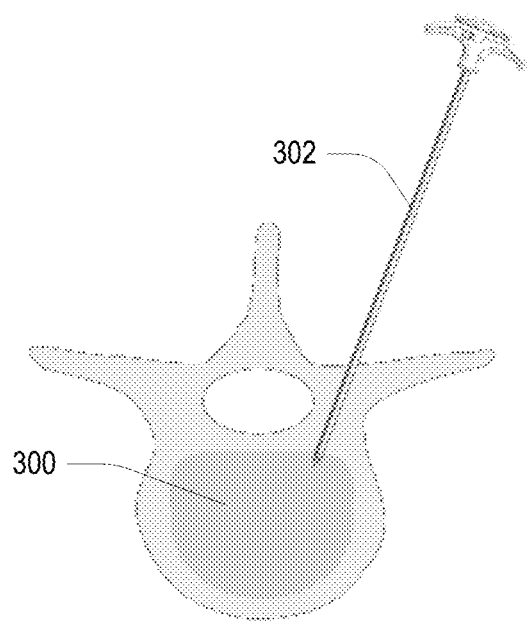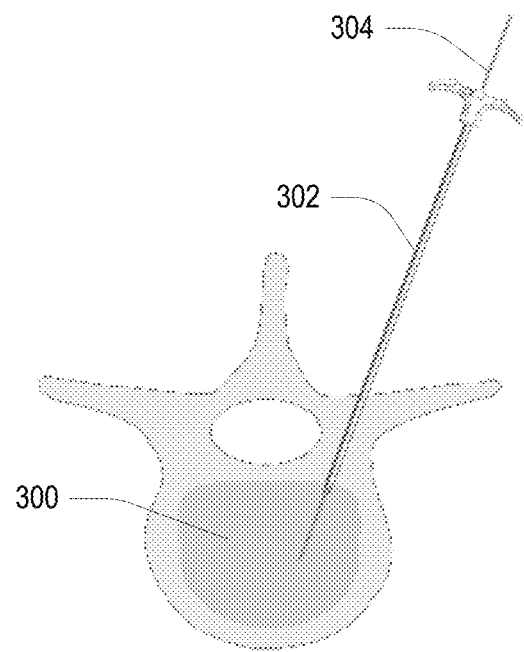
FIG. 3A  FIG. 3B
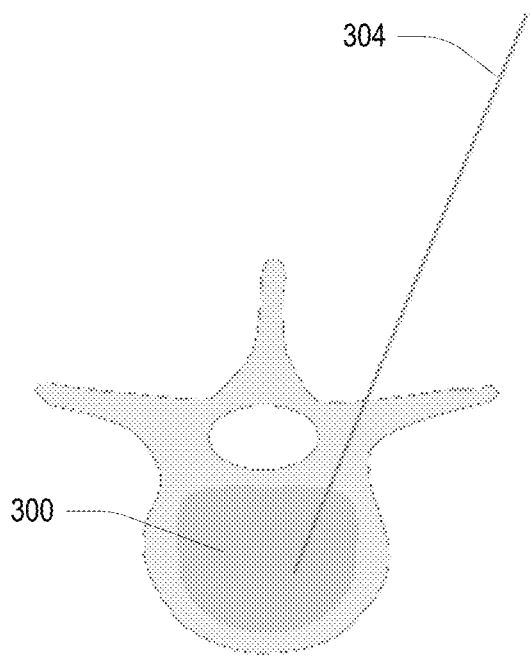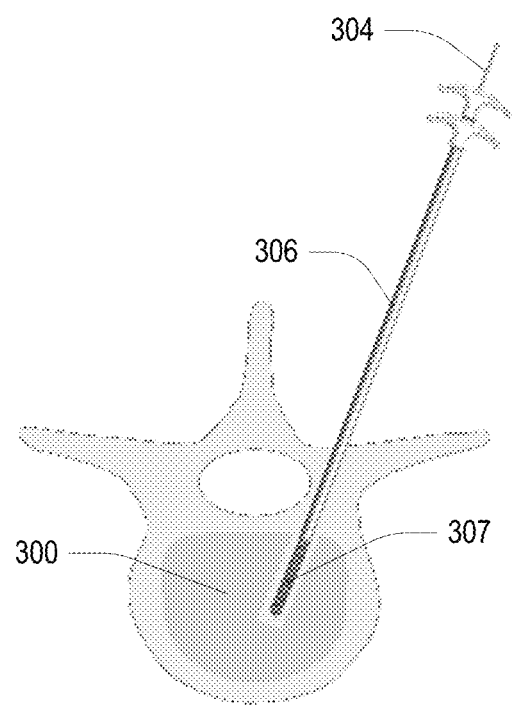
FIG. 3C  FIG. 3D

SPINAL STABILITY SYSTEM

CROSS-REFERENCE TO RELATED APPLICATIONS

The current application is a continuation-in-part of U.S. patent application Ser. No. 18/497,922 filed on Oct. 30, 2023 which, in turn, is a continuation of U.S. patent application Ser. No. 18/087,738 filed on Dec. 22, 2022, the contents of both of which are hereby fully incorporated by reference.

TECHNICAL FIELD

The subject matter described herein generally relates to systems and methods for vertebral operation. More specifically, the subject matter herein relates to treatment of spinal injuries or deformities through vertebral body reconstruction, augmentation, and/or stabilization.

BACKGROUND

Internal spinal fixation devices can be used during spinal surgery to provide stability for injured or damaged vertebrae. For instance, the use of pedicle screw instrumentation has become increasingly widespread for such procedures. Pedicle screws are often inserted through the trabecular bone of the vertebral body to provide stability and to correct vertebral body deformities. Pedicle screw performance is directly related to the strength of attachment to the spine, and failure of pedicle screws is of significant clinical importance to patients. Indeed, pedicle screw loosening is a common complication after spine surgeries.

Relatedly, vertebral augmentation procedures, such as kyphoplasty, are also commonly used to provide stability for injured or damaged vertebrae. Such percutaneous spinal procedures involve bone cement being injected through a small hole in the skin into a collapsed or fractured vertebra. Specifically, kyphoplasty first seeks to restore the height and angle of kyphosis of a fractured vertebrae, and then provides stabilization using injected bone cement. The procedure typically includes the use of a small balloon that is inflated in the vertebral body to create a void within the cancellous bone prior to cement delivery. Once the void is created, the bone cement is then delivered into the newly created void. It is critical that the creation of the void and the bone cement delivery result in the proper height and angular restoration of the vertebral body. However, because the balloon providing the expansion forces within the vertebrae is typically deflated and removed prior to the bone cement being introduced, the volume and/or shape of the void can change. As a result, this multistep process can produce unreliable height and angular modifications to the vertebral body, leading to inconsistent patient outcomes.

SUMMARY

The subject matter described herein provides many technical advantages over the prior art. For instance, in some aspects the methods, devices, and kits described herein provide efficient, minimally invasive solutions to physicians seeking minimally invasive options for vertebral body reconstruction, augmentation, and stabilization in severe osteoporotic and neoplastic fractures, as well as other procedures. Specifically, in some aspects, a fractured or otherwise injured vertebra can be restored to a desired form using bone cement delivered into an expanded metal mesh within a surgical site, which functions to guide the bone cement delivery and helps temporarily maintain a created cavity shape prior to the bone cement hardening. In some aspects, the bone cement is delivered via a fenestrated pedicle screw to the vertebral body, resulting in 360° vertebral internal fixation and thereby minimizing the risk of displacement compared to traditional augmentation techniques. By first stabilizing the vertebral body using an expandable metal mesh delivered by a balloon-tipped cannula, surgical outcomes can be substantially improved.

In one aspect, a spine stabilization method can include inserting, using a cannulated screwdriver, a pedicle screw into a surgical site stabilized by an expandable metal mesh delivered by a balloon-tipped cannula; and supplying bone cement to the surgical site by passing the bone cement through the cannulated screwdriver, wherein the bone cement exits out of at least one fenestration or cannulation of the pedicle screw such that the bone cement in combination with the pedicle screw maintain a desired anatomical distance in the surgical site.

The pedicle screw in the method can include a plurality of fenestrations positioned along the axial direction of the pedicle screw. The pedicle screw can include an expandable balloon covering at least one fenestration, wherein the expandable balloon expands when the bone cement exits the at least one fenestration. The expandable balloon can be dissolvable. The expandable balloon can be connected to the pedicle screw through one or more O-ring seals.

The method can further include controlling the location within the surgical site that the bone cement is supplied. The pedicle screw can include one or more fenestrations arranged in a substantially similar axial direction, and wherein the controlling the location that the bone cement is supplied includes rotating the pedicle screw until the at least one fenestration or cannulation is positioned in a target direction prior to supplying the bone cement. The pedicle screw can include a threaded portion and non-threaded portion having the one or more fenestrations, wherein the non-threaded portion of the pedicle screw is configured to rotate relative to the threaded portion. Controlling the location that the bone cement is supplied can include modifying the position of a cement cannula within the cannulated screwdriver relative to the pedicle screw. The pedicle screw can include an internal divider, the internal divider fluidly separating a first chamber comprising a first fenestration and a second chamber comprising a second fenestration, wherein the cement cannula includes a directional element configured to selectively supply the bone cement to the first chamber, the second chamber, or both chambers.

The surgical site can be located within a vertebral body. The desired anatomical distance can be a predetermined distance representing a height of a vertebral body. The cannulated screwdriver can include a locking mechanism configured to lock the screwdriver at a position along the length of the delivery wire. The bone cement can comprise polymethylmethacrylate (PMMA).

In another aspect, a spine stabilization method can include inserting a wire into a surgical site using a trephine needle having a stylet; overlaying a working sleeve over the wire; creating a cavity inside the surgical site using a cannulated drill passing through the working sleeve; delivering an expandable balloon enclosed by an expandable metal mesh into the cavity through the working sleeve using a balloon-tipped cannula; inflating the balloon until a desired anatomical distance is obtained; deflating the balloon and removing the balloon while maintaining the desired anatomical distance using the expandable metal mesh; inserting a delivery wire through the working sleeve into a lumen of the expandable metal mesh; removing the working sleeve;

inserting a pedicle screw into the surgical site using a cannulated screwdriver guided by the delivery wire, the pedicle screw having at least one fenestration or cannulation;

inserting a cement cannula through the cannulation of the screwdriver; and supplying bone cement to the cavity by passing the bone cement through the cement cannula exiting out of the at least one fenestration or cannulation of the pedicle screw such that the bone cement in combination with the pedicle screw maintain the desired anatomical distance.

The pedicle screw in the method can include a plurality of fenestrations positioned along the axial direction of the pedicle screw. The pedicle screw can include an expandable balloon covering at least a portion of the at least one fenestration or cannulation, wherein the expandable balloon expands when bone cement exits the at least one fenestration or cannulation. The expandable balloon can be dissolvable. The expandable balloon can be connected to the pedicle screw through one or more O-ring seals.

The method can further include controlling the location within the cavity that the bone cement is supplied. The pedicle screw can include one or more fenestrations arranged in a substantially similar axial direction, wherein the controlling the location that the bone cement is supplied includes rotating the pedicle screw until the at least one fenestration or cannulation is positioned in a target direction prior to supplying the bone cement. Controlling the location that the bone cement is supplied can include modifying the position of the cement cannula relative to the pedicle screw. The pedicle screw can include an internal divider, the internal divider fluidly separating a first chamber comprising a first fenestration and a second chamber comprising a second fenestration, wherein the cement cannula includes a directional element configured to selectively supply the bone cement to the first chamber, the second chamber, or both chambers.

The surgical site can be located within a vertebral body. The desired anatomical distance can be a predetermined distance representing a height of a vertebral body. The cannulated screwdriver can include a locking mechanism configured to lock the screwdriver at a position along the length of the delivery wire. The bone cement can comprise polymethylmethacrylate (PMMA). The expandable metal mesh can be configured to expand into a substantially spherical form. The method can further include injecting an imaging agent into the balloon and monitoring the inflation volume of the balloon to determine when the desired anatomical distance is obtained.

In one aspect, a spine stabilization method includes inserting a wire into a surgical site using a trephine needle having an interlocking hub and stylet; overlaying a working sleeve over the wire; creating a cavity inside the surgical site using a drill passing through the working sleeve; delivering an expandable balloon enclosed by an expandable metal mesh into the cavity through the working sleeve using a balloon-tipped cannula; inflating the balloon until a desired anatomical distance is obtained; deflating the balloon and removing the balloon while maintaining the desired anatomical distance using an expandable metal mesh; supplying bone cement into a lumen of the expandable metal mesh.

In another aspect, a kit for performing a spine stabilization procedure can include a balloon-tipped cannula having an expandable balloon enclosed by an expandable metal mesh, the balloon-tipped cannula configured to pass through a working sleeve and to expand the expandable balloon and expandable metal mesh within a surgical site; and a pedicle screw having at least one fenestration or cannulation which is configured to be inserted into the surgical site.

The kit can further include an injection system configured to supply bone cement to the surgical site through the at least one fenestration or cannulation of the pedicle screw when the pedicle screw is positioned within the injection site. The injection system can include a bone cement cannula configured to be inserted through a cannulated screwdriver. The kit can further include one or more additional pedicle screws, wherein each pedicle screw has a different axial length. The kit can further include a source of bone cement. The kit can further include an inflation device configured to apply an expansion pressure to the balloon-tipped cannula.

In one aspect, a screwdriver system can include a cannulated tubular body; a pedicle screw coupling positioned at a first end of the cannulated tubular body, the pedicle screw coupling configured to couple to a pedicle screw in a manner that the pedicle screw can be driven while the pedicle screw coupling is rotated; and a cement cannula positioned within the cannulated tubular body, the cement cannula configured to supply bone cement to a coupled pedicle screw through the cannulation of the tubular body.

The cement cannula can be configured to remain within the cannulated tubular body while the pedicle screw coupling is rotated. The screwdriver system can further include a cement cannula port connected to the cement cannula. The cement cannula can include a directional element configured to selectively supply bone cement to a pedicle screw attached to the pedicle screw coupling. The cement cannula can include a directional element configured to selectively supply the bone cement to the pedicle screw in an adjustable direction. The pedicle screw coupling can include a cutting element, the cutting element configured to provide access to a surgical site. The screwdriver system can further include a handle connected to a second end of the cannulated tubular body.

In another aspect, a screwdriver system can include a cannulated tubular body; a pedicle screw coupling positioned at a first end of the cannulated tubular body, the pedicle screw coupling configured to couple to a pedicle screw in a manner that the pedicle screw can be driven while the pedicle screw coupling is rotated; a handle attached to a second end of the cannulated tubular body; an internal shaft positioned within the cannulated tubular body, the internal shaft having a threaded portion which protrudes from the first end of the cannulated tubular body, and a handle knob positioned within at least a portion of the handle, the handle knob being connected to the internal shaft in a manner wherein rotating the handle knob produces a rotation in the threaded portion of the internal shaft.

The threaded portion can be configured to be screwed into a pedicle screw, thereby forming an attachment between the internal shaft and the pedicle screw. The pedicle screw coupling can include a cutting element, the cutting element configured to provide access to a surgical site. The handle can include at least one aperture configured to provide access to the handle knob. The handle knob can be substantially enclosed by the handle. At least a portion of the handle knob can partially protrude through the aperture and extend beyond a face of the handle. The handle knob can include a circular body having a flat top surface, a flat bottom surface, and a circular side wall. The circular side wall can include a plurality of ridges arranged in an axial direction relative to the cannulated tubular body. The circular body can include a central aperture configured to provide access from the top surface to the bottom surface. The handle can include a first handle arm and a second handle arm, the first and the second handle arms extending outward in opposite radial directions relative to the cannulated tubular body. The first handle arm and the second handle arm can each have an exterior end and an interior end, wherein the widths of the each handle arm at the exterior ends is smaller than the widths at the interior ends.

In one aspect, a pedicle screw for use in a spine stabilization procedure can include a cylindrical body; a threaded portion positioned along at least a part of the cylindrical body; a drill coupling member positioned at a first end of the cylindrical body; a first fenestration positioned along the cylindrical body; a second fenestration positioned along the cylindrical body; and an internal divider fluidly separating a first chamber comprising the first fenestration and a second chamber comprising the second fenestration, wherein the internal divider is configured to ensure bone cement introduced into the first chamber only exits out of the first fenestration and bone cement introduced into the second chamber only exits out of the second fenestration.

The internal divider can include an internal cannulation configured to receive a wire passing through the pedicle screw. The internal cannulation can be fluidly separated from the first chamber and the second chamber. The first fenestration and the second fenestration can be positioned at the same axial position on opposite sides of the cylindrical body. The pedicle screw can include at least two additional fenestrations positioned along the cylindrical body. The pedicle screw can be threaded along the entire length of the cylindrical body. The drill coupling can include a hexalobular socket.

In another aspect, a pedicle screw for use in a spine stabilization procedure can include a cylindrical body; a threaded portion positioned along at least a part of the cylindrical body; a drill coupling member positioned at a first end of the cylindrical body; a first fenestration positioned along the cylindrical body; and an expandable balloon attached to the cylindrical body and covering the first fenestration, wherein the expandable balloon is configured to expand when bone cement exits the first fenestration.

The expandable balloon can be dissolvable. The expandable balloon can be connected to the pedicle screw through one or more O-ring seals. The pedicle screw can include at least one additional fenestration positioned along the cylindrical body. The drill coupling can include a hexalobular socket.

In one aspect, a device for a spinal stabilization procedure is provided. The device can include a cannulated tubular body having a first end configured to be inserted into a surgical site and a second end. The device can also include an expansion component coupled to the cannulated tubular body. The expansion component can include a plurality of elongated mechanical supports which are configured to be axially aligned with the cannulated tubular body when in a collapsed state, and further configured to bend outward in a radial direction when in an expanded state.

In another aspect, a pedicle screw for use in a spine stabilization procedure is provided. The pedicle screw can include a cannulated tubular body having a first end configured to be inserted into a surgical site and a second end, a threaded cover positioned over the second end which is configured to be secured to a bone within a surgical site, and an expansion component coupled to the cannulated tubular body. The expansion component can include a plurality of elongated mechanical supports which are configured to be axially aligned with the cannulated tubular body when in a collapsed state, and further configured to bend outward in a radial direction when in an expanded state.

In one aspect, a device for a spinal stabilization procedure is provided. The device can include a cannulated tubular body having a first end configured to be inserted into a spinal surgical site, and an expansion component coupled to the cannulated tubular body. The expansion component can include a plurality of elongated mechanical supports configured to be axially aligned with the cannulated tubular body when in a collapsed state, and further configured to bend outward in a radial direction when in an expanded state. The expansion component can further include a plug positioned within the cannulated tubular body which is configured to move in an axial direction and to contact and apply a force to the mechanical supports such that movement of the adjustment element toward the first end of the cannulated tubular body shifts the mechanical supports from the collapsed state to the expanded state.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIGS. 3A-3D depict progressive stages of a spine stabilization procedure wherein a balloon-tipped cannula is inserted into a surgical site. FIG. 3A depicts a trephine needle inserted into the surgical site. FIG. 3B depicts a wire inserted into the surgical site through the trephine needle after a stylet of the trephine needle has been removed. FIG. 3C depicts the wire inserted into the surgical site after the hub of the trephine needle has been removed. FIG. 3D depicts a cannulated drill inserted into the surgical site through a working sleeve.

FIG. 4A depicts a balloon tipped cannula inserted into a surgical site through a working sleeve, wherein the expandable balloon is enclosed by an expandable metal mesh. FIG. 4B depicts the balloon and the expandable metal mesh in an expanded form within the surgical site. FIG. 4C depicts the expandable metal mesh in an expanded form within the surgical site after the balloon tipped cannula has been removed and replaced with a delivery wire. FIG. 4D depicts the delivery wire inserted into the surgical site after the working sleeve has been removed.

FIG. 5A depicts a pedicle screw inserted into a lumen of the expandable metal mesh in the surgical site by a cannulated screwdriver guided by the delivery wire. FIG. 5B depicts a cement cannula having replaced the delivery wire, wherein bone cement has been supplied to the surgical site through cement cannula and the pedicle screw.

The current subject matter will be better understood by reference to the following detailed description when considered in combination with the accompanying drawings which form part of the present specification.

DETAILED DESCRIPTION

As used herein, "bone cement" generally refers to any suitable clinically-approved bone stabilization or replacement material that can be injected into a subject. For example, bone cement can comprise a polymer such as polymethylmethacrylate (PMMA) or a polymer mixture formed substantially thereof. The bone cement can comprise calcium phosphate, magnesium phosphate, or a comparable compound. The bone cement can be limited to compounds which have been approved by the U.S. Food and Drug Administration (FDA) for use in spinal procedures.

As used herein, "trephine needle" generally refers to a needle having a cylindrical blade. A trephine needle can specifically be a hollow, cylindrical needle with a tapered cutting tip. For example, a trephine needle can be a Jamshidi® needle or comparable insertion device.

The methods, devices, and kits of the present disclosure are primarily discussed as being intended for human spinal procedures such as reduction of fractures and vertebral body reconstruction, augmentation, and stabilization in severe osteoporotic and neoplastic fractures of the thoracic lumbar and spine. However, it should be readily appreciated that the teachings described herein can be applied to additional procedures involving alternative surgical sites, including but not limited to, procedures involving bones outside of the vertebral column.

Figure 1:
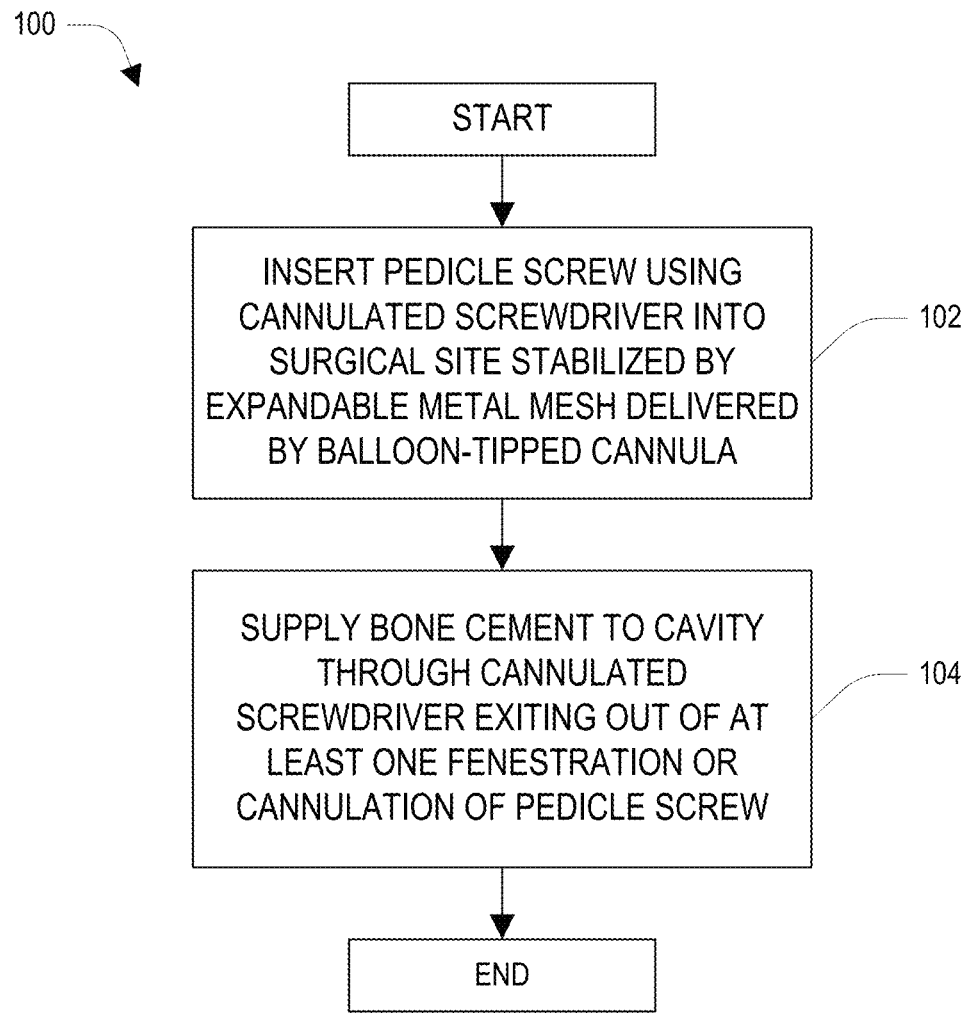
FIG. 1 is a first process flow diagram illustrating a spine stabilization procedure.

FIG. 1 depicts a process flowchart of a spine stabilization procedure 100 in which, at 102, a pedicle screw can be inserted into a surgical site stabilized by an expandable metal mesh delivered by a balloon-tipped cannula. The pedicle screw can be delivered using a cannulated screwdriver. Subsequently, at 104, bone cement can be supplied to the surgical site by passing the bone cement through the cannulated screwdriver exiting out of at least one fenestration or cannulation of the pedicle screw such that the bone cement in combination with the pedicle screw maintain a desired anatomical distance in the surgical site. In this manner, the spine stabilization procedure 100 can provide stability to the surgical site through the combined delivery of both a pedicle screw and the bone cement, so that the desired anatomical distance can be maintained. The spine stabilization procedure 100 can, in some variations, be performed without requiring any guide wires to be inserted into the surgical site.

Figure 2:
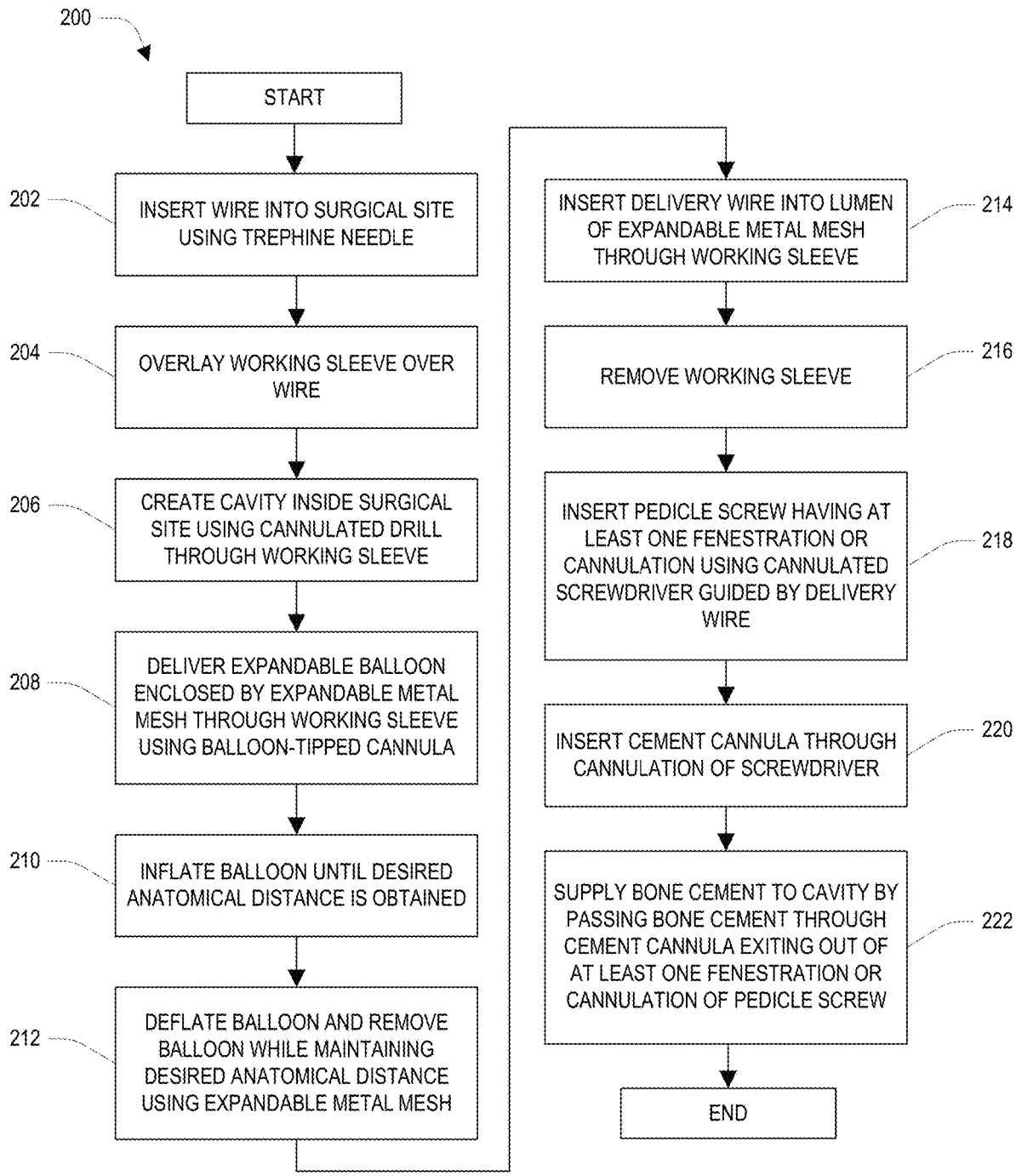
FIG. 2 is a process flow diagram illustrating a spine stabilization procedure.

FIG. 2 depicts a process flowchart of another spine stabilization procedure 200 in which, at 200, a wire can be inserted into a surgical site using a trephine needle having a stylet. Subsequently, at 204, a working sleeve can be overlayed over the wire. Next, at 206, a cavity can be created inside the surgical site using a cannulated drill passing through the working sleeve. Subsequently, at 208, an expandable balloon enclosed by an expandable metal mesh can be delivered into the cavity through the working sleeve using a balloon-tipped cannula. In this manner, the spine stabilization procedure 200 can function to introduce the balloon-tipped cannula into the surgical site in a precise manner. Subsequently, at 210, the balloon can be inflated until a desired anatomical distance is obtained. Next, at 212, the balloon can be deflated and removed while maintaining the desired anatomical distance using the expandable metal mesh. Subsequently, at 214, a delivery wire can be inserted through the working sleeve into a lumen of the expandable metal mesh. Subsequently, at 216, the working sleeve can be removed. At this point in the spine stabilization procedure 200, the desired anatomical distance has been obtained through the inflation of the balloon in the surgical site, and a delivery wire has been introduced in order to guide the introduction of additional items to the surgical site. Next, at 218, a pedicle screw can be inserted into the surgical site using a cannulated screwdriver guided by the delivery wire, the pedicle screw having at least one fenestration or cannulation. Subsequently, at 220, a cement cannula can be inserted through the cannulation of the screwdriver. Next, at 222, bone cement can be supplied to the cavity by passing the bone cement through the cement cannula exiting out of the at least one fenestration or cannulation of the pedicle screw such that the bone cement in combination with the pedicle screw maintain the desired anatomical distance.

The surgical site of the devices, methods, and kits discussed herein can be located within subsection of a vertebral body. The surgical site can be specifically within cancellous bone of a vertebral body. The surgical site can be a target location predetermined by a physician in advance of the procedure using known imaging systems and techniques. The surgical site can be selected as a position within the vertebral body such that, if the surgical site is expanded, the form of the vertebral body will be altered into a desired corrected form.

The desired anatomical distance of the devices, methods, and kits discussed herein can be a measurable length, width, height, or angular position of a vertebral body. In particular, the anatomical distance can be an original height of a vertebral body, prior to a compression fracture or other injury. Alternatively, the desired anatomical distance can be a height of a vertebral body which is predetermined to provide a desired angle of kyphosis or lordosis within a subject. The desired anatomical distance can be predetermined using known imaging systems and techniques prior to conducting the spine stabilization procedure.

The methods described herein can further involve controlling the location within the surgical site that the bone cement is supplied. By controlling where the bone cement is released within the surgical site, a physician can better control the ultimate distribution of the bone cement. This control can be achieved using a variety of different techniques. For instance, an inserted pedicle screw can include one or more fenestrations arranged in a substantially similar axial direction, and controlling the location that the bone cement is supplied can include rotating the pedicle screw until the at least one fenestration or cannulation is positioned in a target direction prior to supplying the bone cement. Using such a technique, the bone cement can be released from the pedicle screw in controlled directional manner. In order to assist a physician during operation, the pedicle screw can include a directional marker or identifier from which the substantially similar axial direction can be discerned, even when the pedicle screw has been substantially inserted into the surgical site.

Alternatively, the controlling the location that the bone cement is supplied can include modifying the position of a cement cannula within the cannulated screwdriver relative to the pedicle screw. For instance, the pedicle screw can include an internal divider, the internal divider fluidly separating a first chamber comprising a first fenestration and a second chamber comprising a second fenestration, wherein the cement cannula includes a directional element configured to selectively supply the bone cement to the first chamber, the second chamber, or both chambers. The directional element can change from supplying cement from one chamber to the other by an active step of, for example, rotating the cement cannula within the cannulated screwdriver.

The methods described herein can involve monitoring the position of at least one of the expandable balloon, the pedicle screw, or the created cavity within the surgical site. For example, the methods can involve injecting an imaging agent into the balloon, and monitoring the inflation volume of the balloon to determine when the desired anatomical distance has been obtained. Imaging devices and techniques commonly known in the art can be employed, including but not limited to, fluoroscopy.

Consistent with some aspects of method 100 and method 200, FIGS. 3A-3D, 4A-4D, 5A-5B illustrate progressive stages of spine stabilization procedures. In particular, these diagrams depict stages associated with a balloon-tipped cannula being inserted into a surgical site, the balloon-tipped cannula being expanded within the surgical site, and bone cement being supplied through a pedicle screw to a surgical site that has been stabilized by an expandable metal mesh. Although directed to stages of related surgical procedures, FIGS. 3A-3D, 4A-4D, 5A-5B do not necessarily illustrate one continuous method, but rather surgical milestones that can be reached using some aspects of the methods described herein.

FIG. 3A depicts a trephine needle 302 inserted into a surgical site 300. The trephine needle can function to create an initial entry point to the surgical site 300. In this depiction, the surgical site 300 is within a vertebral body and the trephine needle 302 has been inserted through the pedicle bone. FIG. 3B depicts a wire 304 inserted into the surgical site 300 through the trephine needle 302 after the stylet of the trephine needle 302 has been removed. FIG. 3C depicts the wire 304 inserted into the surgical site 300 after the trephine needle 302 has been removed. FIG. 3D depicts a cannulated drill 307 inserted into the surgical site 300 through a working sleeve 306. The wire 304 can function to guide the cannulated drill 307 to the surgical site 300, where the cannulated drill 307 is then used to form a cavity within the surgical site 300.

Figure 4A:
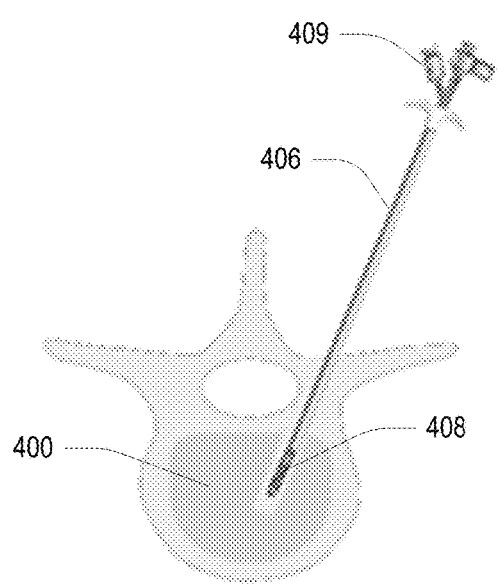
FIGS. 4A-4D depict progressive stages of a spine stabilization procedure wherein a balloon-tipped cannula is expanded within a surgical site.
Figure 4B:
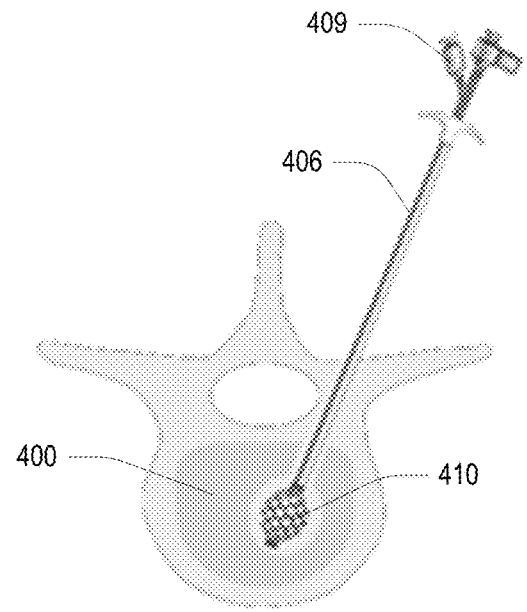
Figure 4C:
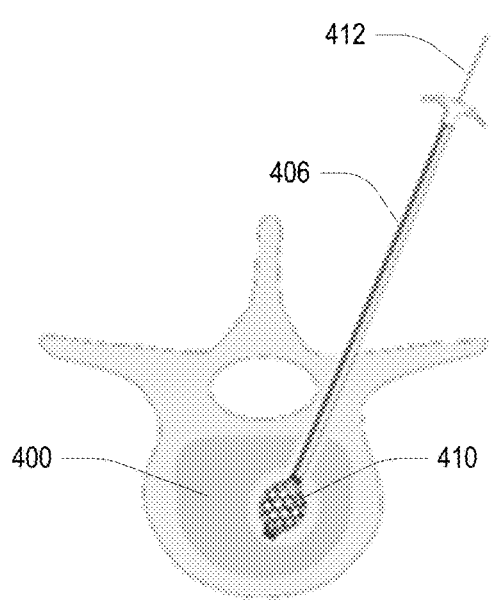
Figure 4D:
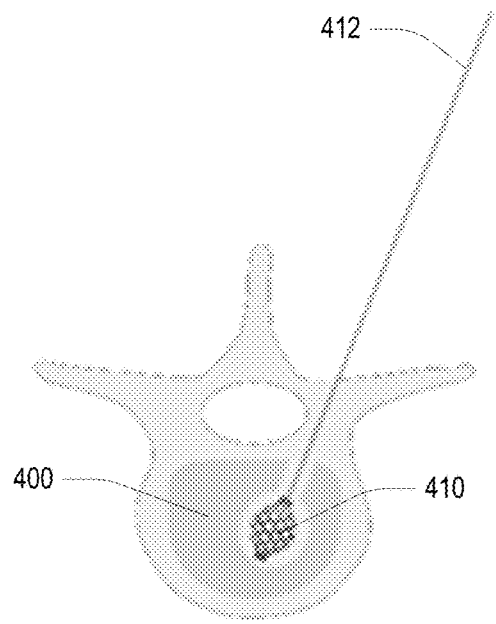

FIG. 4A depicts a balloon tipped cannula 409 with an expandable balloon 408 inserted into a cavity in a surgical site 400 through a working sleeve 406, wherein the expandable balloon 408 is enclosed by an expandable metal mesh. FIG. 4B depicts the balloon and the expandable metal mesh in an expanded form 410 within the expanded cavity of the surgical site 400. FIG. 4C depicts the expandable metal mesh in an expanded form 410 within the surgical site 400 after the balloon tipped cannula 409 has been removed and replaced with a delivery wire 412. FIG. 4D depicts the delivery wire 412 still inserted into the surgical site 400 after the working sleeve 406 has been removed.

Figure 5A:
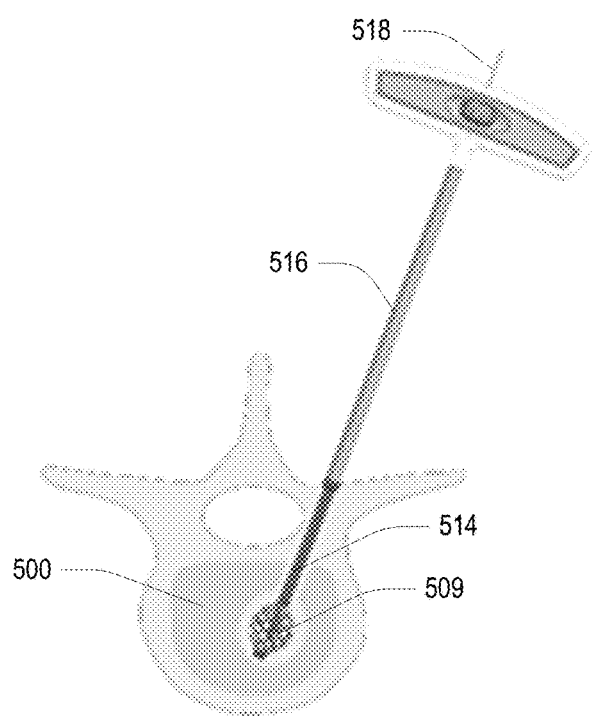
FIGS. 5A-5B depict progressive stages of a spine stabilization procedure wherein bone cement is supplied to a surgical site.
Figure 5B:
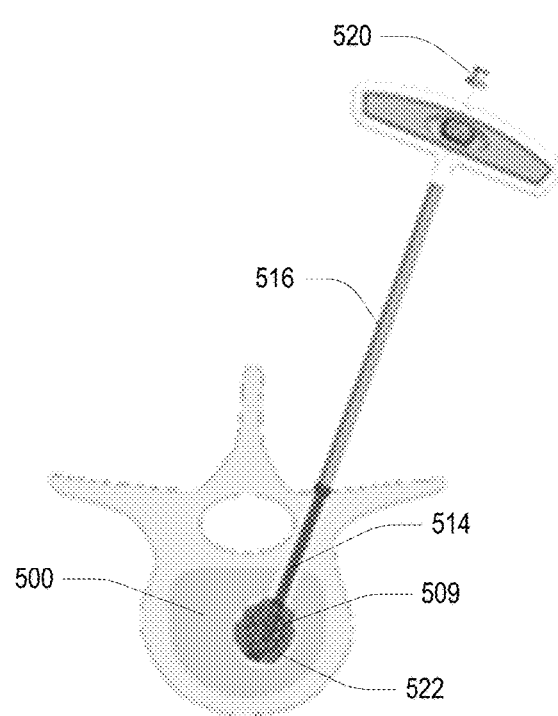

FIG. 5A depicts a pedicle screw 514 inserted into a lumen of an expanded metal mesh 509 in the surgical site 500. The pedicle screw 514 has been inserted using a cannulated screwdriver 516 guided by the delivery wire 518. FIG. 5B depicts a cement cannula 520 having replaced the delivery wire 518 within the cannulated screwdriver 516, wherein bone cement 522 has been supplied to the surgical site 500 through cement cannula 520 and the pedicle screw 514.

Figure 6:
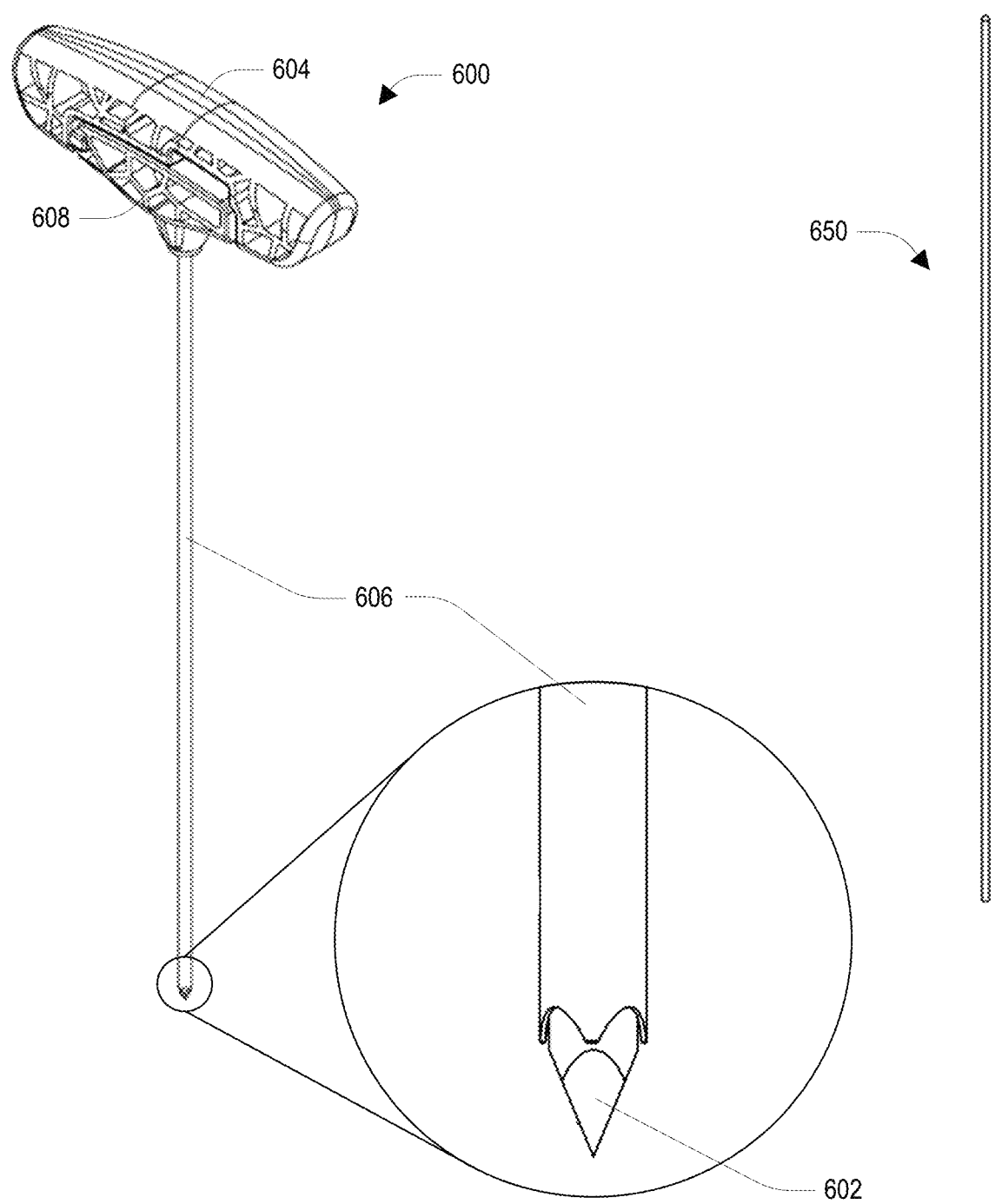
FIG. 6 depicts an isometric view of a trephine needle and an associated surgical wire.

FIG. 6 depicts an exemplary trephine needle 600 and an associated wire 650, which can be utilized in the systems and methods described herein. The trephine needle 600 can include a removable stylet 602 connected to a first detachable hub segment 604. When attached, the removable stylet 602 can be positioned within a sleeve 606 connected to a second hub segment 608. In this manner, the trephine needle 600 can be configured to access a surgical site, at which point the stylet 602 and first detachable hub segment 604 can be removed, and the associated wire 650 can be inserted into the sleeve 606. Suitable trephine needles for use in accordance with the systems and methods described herein include, but are not limited to, Jamshidi® needles and other comparable biopsy needles. The trephine needle 600 can be formed of a high-strength, biocompatible material, such as stainless steel. The wire 650 can be formed of stainless-steel or a comparable material, and can be configured to guide a cannulated drill once inserted into a surgical site. The wire 650 can specifically be a stainless-steel Kirschner wire.

Figure 7:
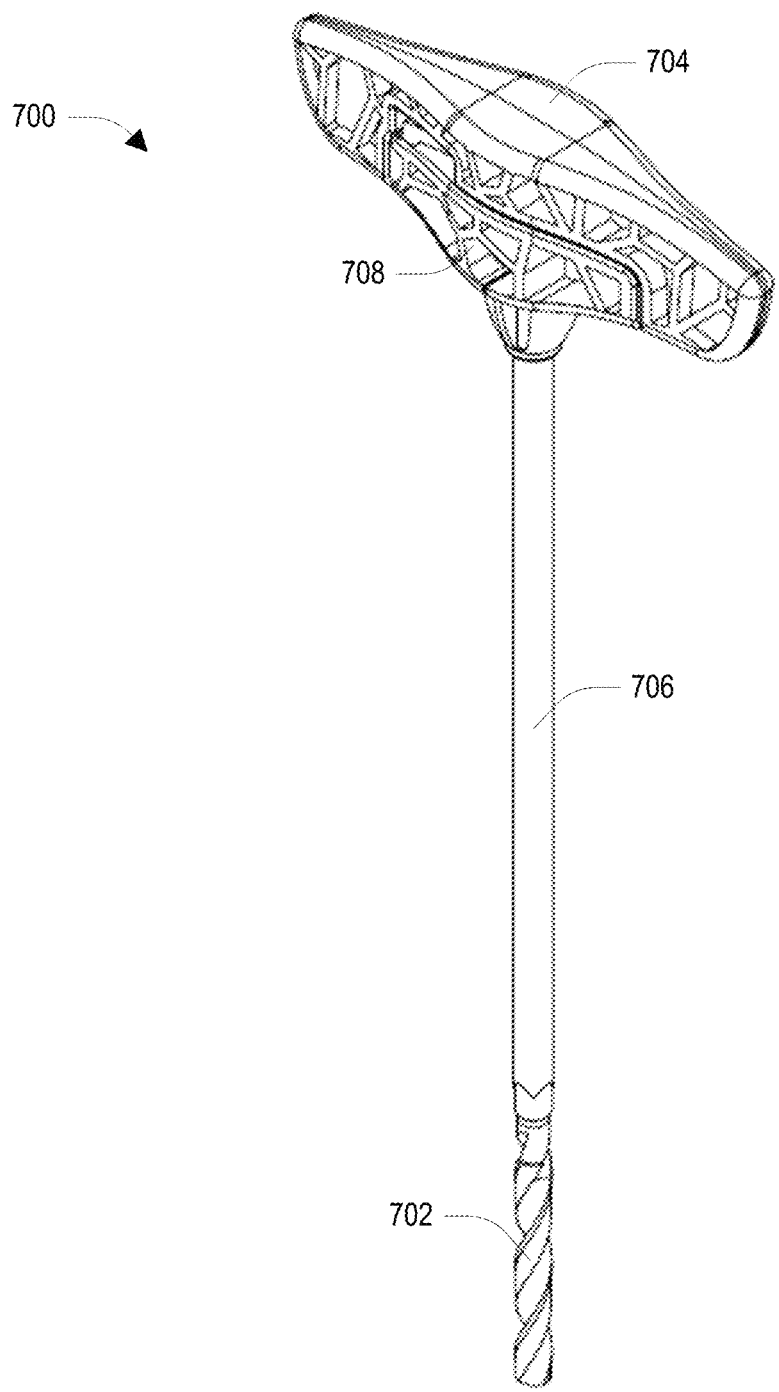
FIG. 7 depicts an isometric view of a cannulated drill having a working sleeve.

FIG. 7 depicts an exemplary cannulated drill 700, which can be utilized in the systems and methods described herein. The cannulated drill 700 can have a reamer bit 702 connected to a first detachable drill segment 704. When attached, the reamer bit 702 and detachable drill segment 704 can be positioned within a working sleeve 706 connected to a second drill segment 708. In this manner, the cannulated drill 700, being guided by an inserted wire, can be configured to create a cavity in a surgical site, at which point the reamer bit 702 and detachable drill segment 704 can be removed. As a result, access to the created cavity through the working sleeve 706 can be thereby provided.

Figure 8:
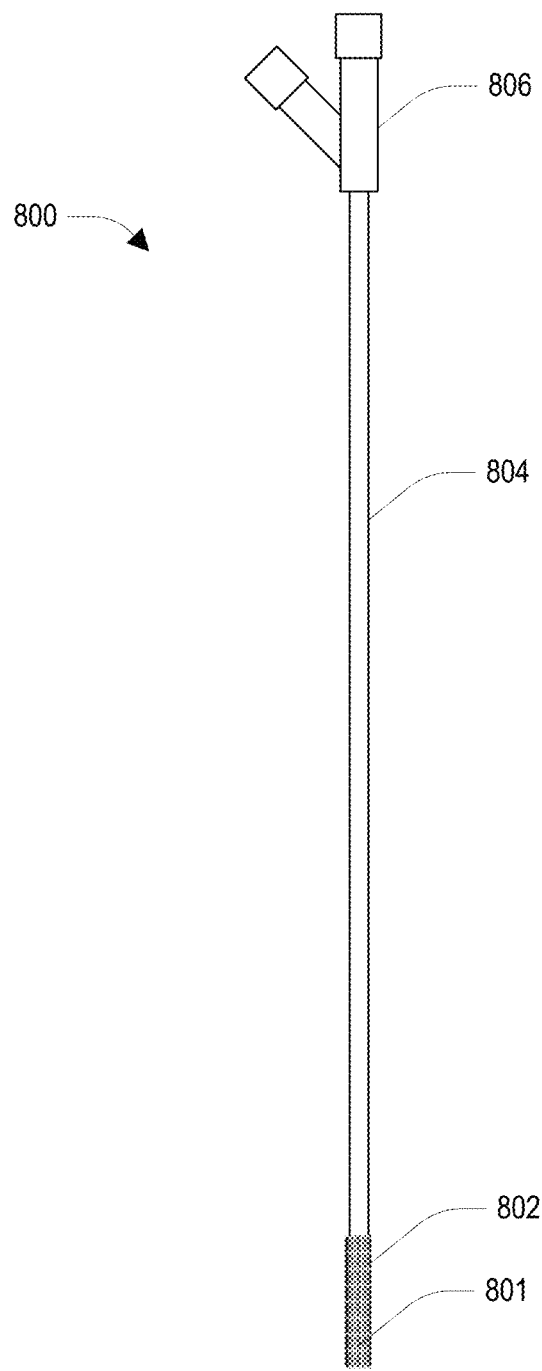
FIG. 8 depicts a front view of balloon-tipped cannula with an expandable metal mesh.
Figure 9A:
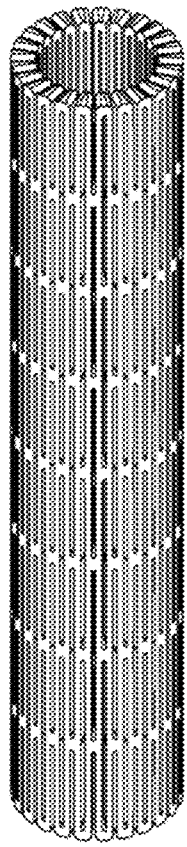
FIG. 9A depicts an isometric view of an expandable metal mesh in a collapsed form.
Figure 9B:
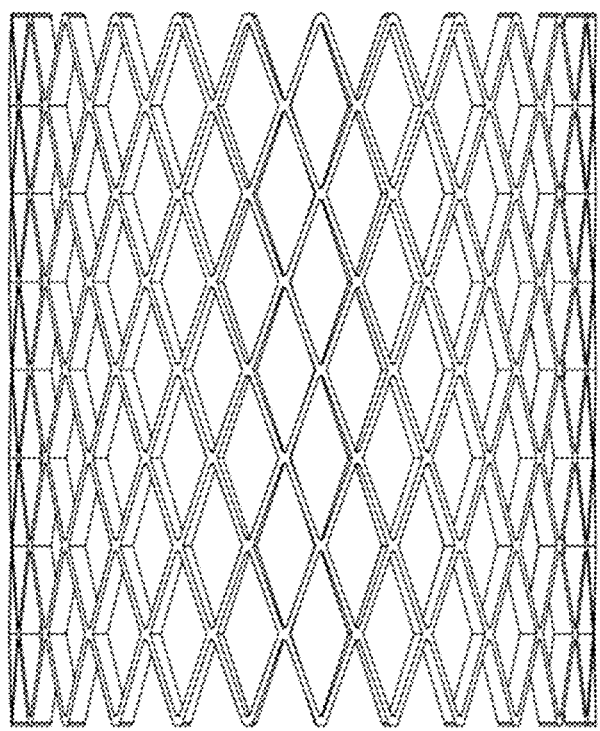
FIG. 9B depicts a front view of the expandable metal mesh of FIG. 9A in an expanded form.
Figure 10A:
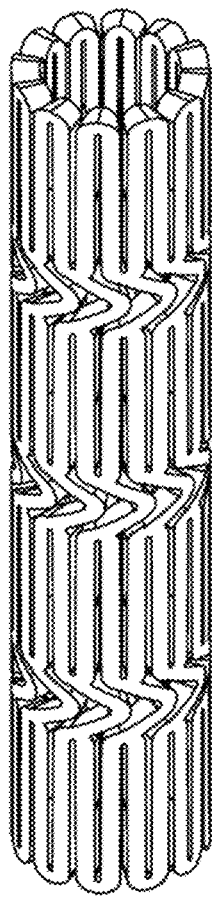
FIG. 10A depicts an isometric view of an expandable metal mesh in a collapsed form.
Figure 10B:
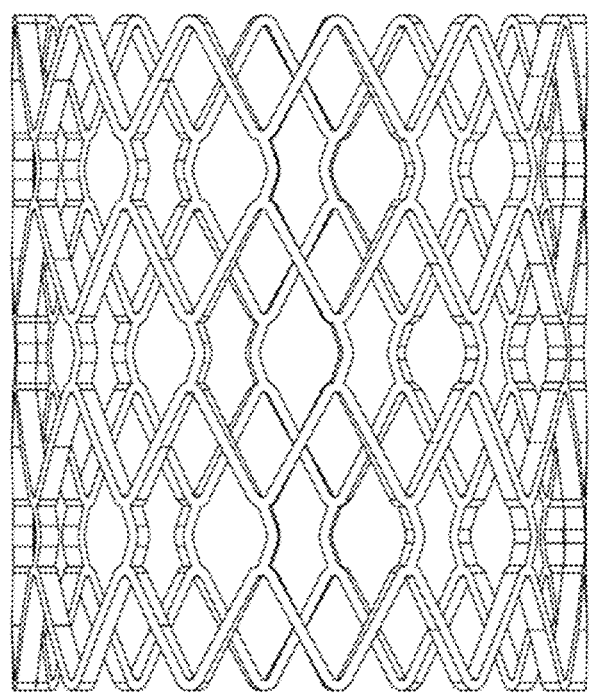
FIG. 10B depicts a front view of the expandable metal mesh of FIG. 10A in an expanded form.

FIG. 8 depicts an exemplary balloon-tipped cannula 800 with a balloon 801 and an associated expandable metal mesh 802, which can be utilized in the systems and methods described herein. The balloon-tipped cannula 800 can include a cannula body 804 connecting the balloon 801 to a cannula port 806. In this manner, an inflation device such as a pump or syringe can fluidly connect to the cannula port 806 and be used to expand the balloon 801. The cannula port 806 can utilize any suitable connector, including, but not limited to Luer fittings. With the exception of the cannula port 806, the balloon-tipped cannula 800, when in a compressed form can be sized to fit within a working sleeve and cavity positioned within a vertebral body. The balloon 801 can be formed of an expandable material, such as a biocompatible polymer.

FIGS. 9A-9B, 10A-10B depict various configurations for expandable metal meshes, which can be utilized in the systems and methods described herein. As shown, the expandable metal meshes can be formed of different patterns depending on the necessary mechanical requirements of a given surgical site. Although the expandable metal meshes are depicted as cylindrical constructions, alternative expanded forms are possible, such as substantially spherical or boxed forms. The expandable metal mesh can be formed of an inelastic material capable of expanding and maintaining its expanded form. The expandable metal mesh can be formed of a metal, and can specifically be cobalt chromium. The expandable metal mesh can be available in different sizes, depending on the particular surgical site and desired anatomical distance. Relatedly, the methods described herein can further involve selecting a properly sized expandable metal mesh for a particular surgical site. In particular, in order to fit within the working sleeve and a cavity of a target site, the expandable metal mesh, when in an unexpanded form, can have a diameter between 10 millimeters and 20 millimeters and/or a length between 10 millimeters and 30 millimeters.

Figure 11:
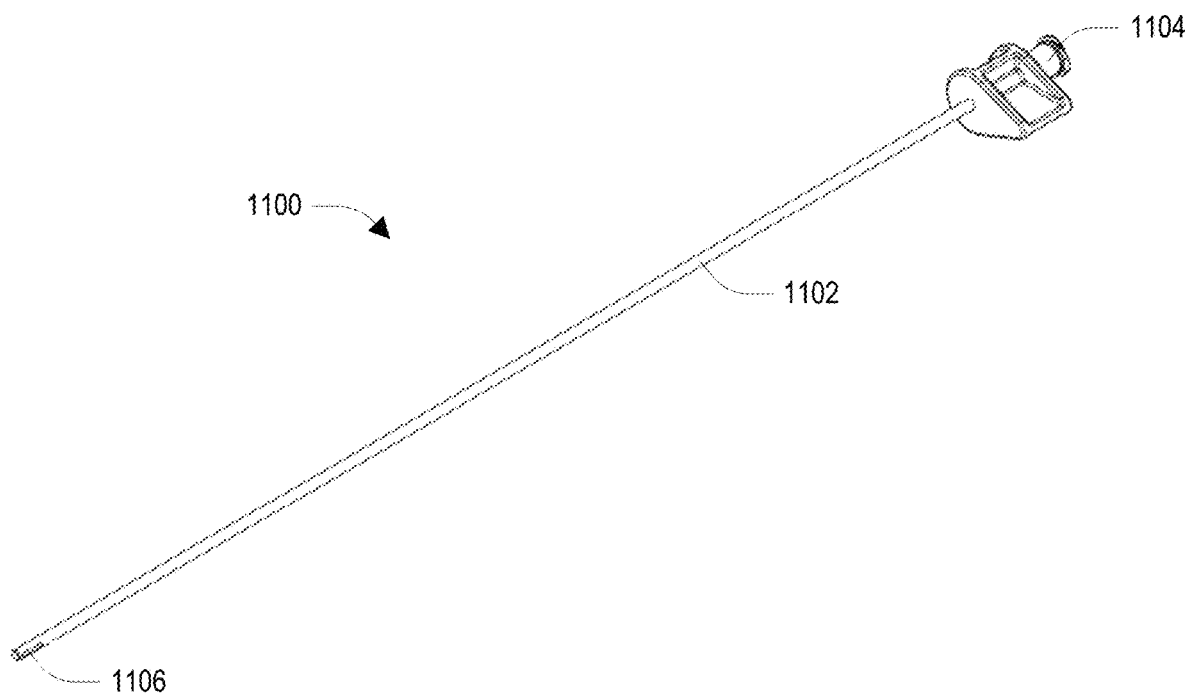
FIG. 11 depicts an isometric view of a bone cement cannula.

FIG. 11 depicts an exemplary bone cement cannula 1100, which can be utilized in the systems and methods described herein. The bone cement cannula 1100 can include a cannula body 1102 fluidly connecting an external port 1104 on a first end and a delivery aperture 1106 on a second end. The bone cement cannula 1100 can thereby be configured to supply bone cement to a surgical site by passing the bone cement through the external port 1104 and the cannula body 1102, wherein the bone cement exits out of the delivery aperture 1106. The delivery aperture 1106 can include a directional element such as the one shown, wherein the aperture is located on one side of the cannula body 1102. Alternatively, the delivery aperture 1106 can be positioned on the base of the cannula tubular body 1102 and can be configured to provide a substantially uniform distribution of bone cement in the axial direction. With the exception of the external port 1104, the bone cement cannula 1100 can be sized to fit within a working sleeve inserted into a surgical site. Furthermore, the second end of the cannula body 1102 can be sized to fit within the lumen of a cannulated pedicle screw. The bone cement cannula 1100 can have an interior tube, wherein the interior tube is configured to prevent bone cement delivered through the cannula body 1102 from contacting a wire within the interior tube, such as a delivery wire inserted into a surgical site.

Figure 12A:
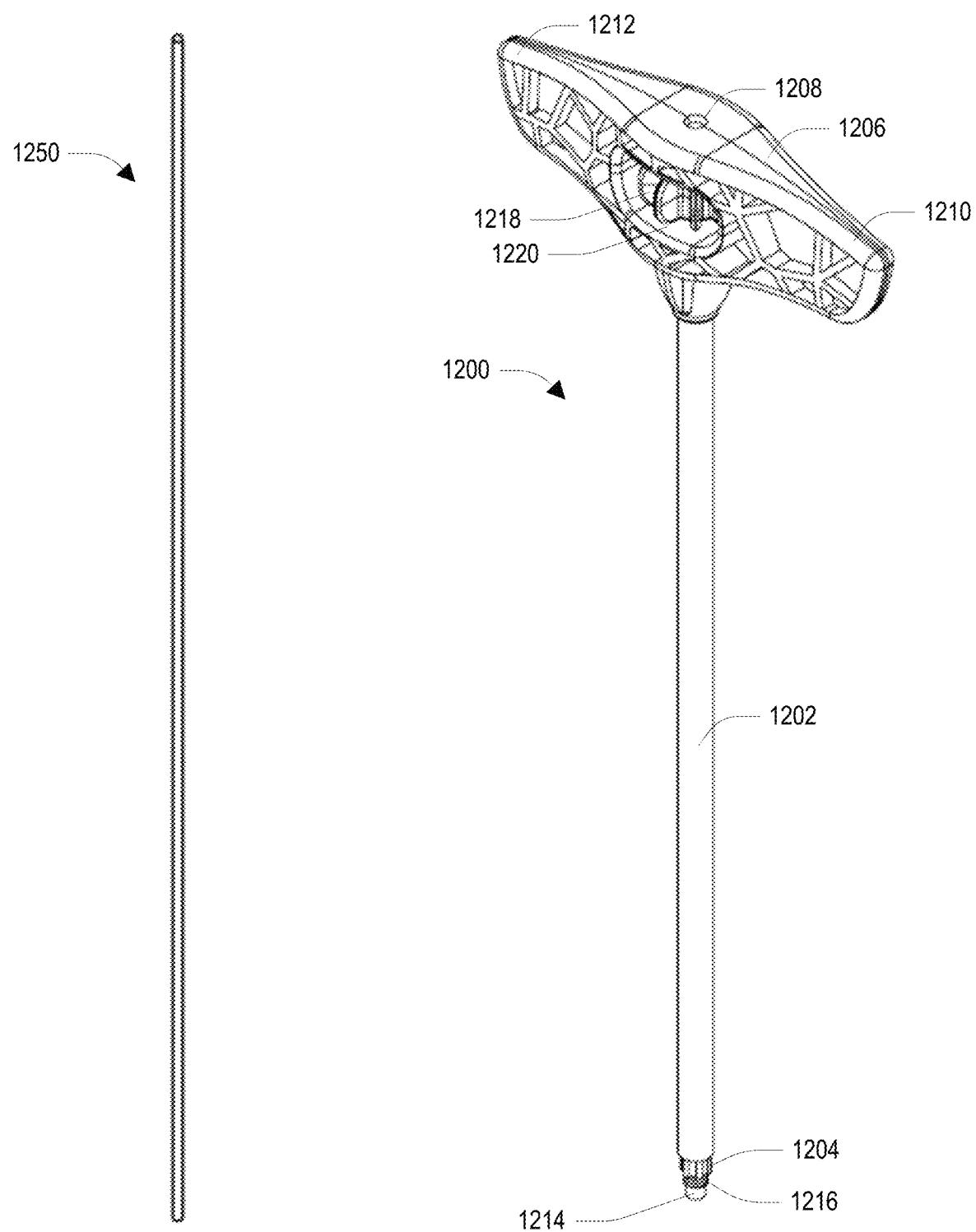
FIG. 12A depicts an isometric view of a cannulated screwdriver and an associated wire.

FIG. 12A depicts an exemplary cannulated screwdriver 1200 and an associated delivery wire 1250, which can be utilized in the systems and methods described herein. The cannulated screwdriver 1200 can include a cannulated tubular body 1202. The cannulated tubular body 1202 can have a length and diameter specifically selected to fit into a cavity of surgical site. The screwdriver system 1200 can also include a pedicle screw coupling member 1204 attached to a first end of the cannulated tubular body 1202 and a handle 1206 connected to a second end of the cannulated tubular body 1202 and having a first handle arm 1210 and a second handle arm 1212 extending outward in opposite radial directions relative to the cannulated tubular body. The first handle arm 1210 and the second handle arm 1212 each have an exterior end and an interior end, wherein the widths of the each handle arm at the exterior ends is smaller than the widths at the interior ends. In this manner, the center of the handle 1206 can be thicker to provide structural stability and support the handle knob 1218. The pedicle screw coupling member 1204 can be configured to couple to a pedicle screw in a manner that the pedicle screw can be driven while the pedicle screw coupling member 1204 is rotated.

The cannulated screwdriver 1200 can also have an internal shaft 1214 positioned within the cannulated tubular body 1202. The internal shaft 1214 can have a threaded portion 1216 which protrudes from the first end of the cannulated tubular body 1202. A handle knob 1218 can be positioned within an aperture 1220 of the handle. Specifically, the handle knob can be substantially enclosed by the handle, with at least a portion of the handle knob partially protruding through the aperture and extending beyond a face of the handle. The handle knob 1218 can be connected to the internal shaft so that a rotation of the handle knob 1218 produces a rotation in the threaded portion 1216 of the internal shaft 1214.

Figure 12B:
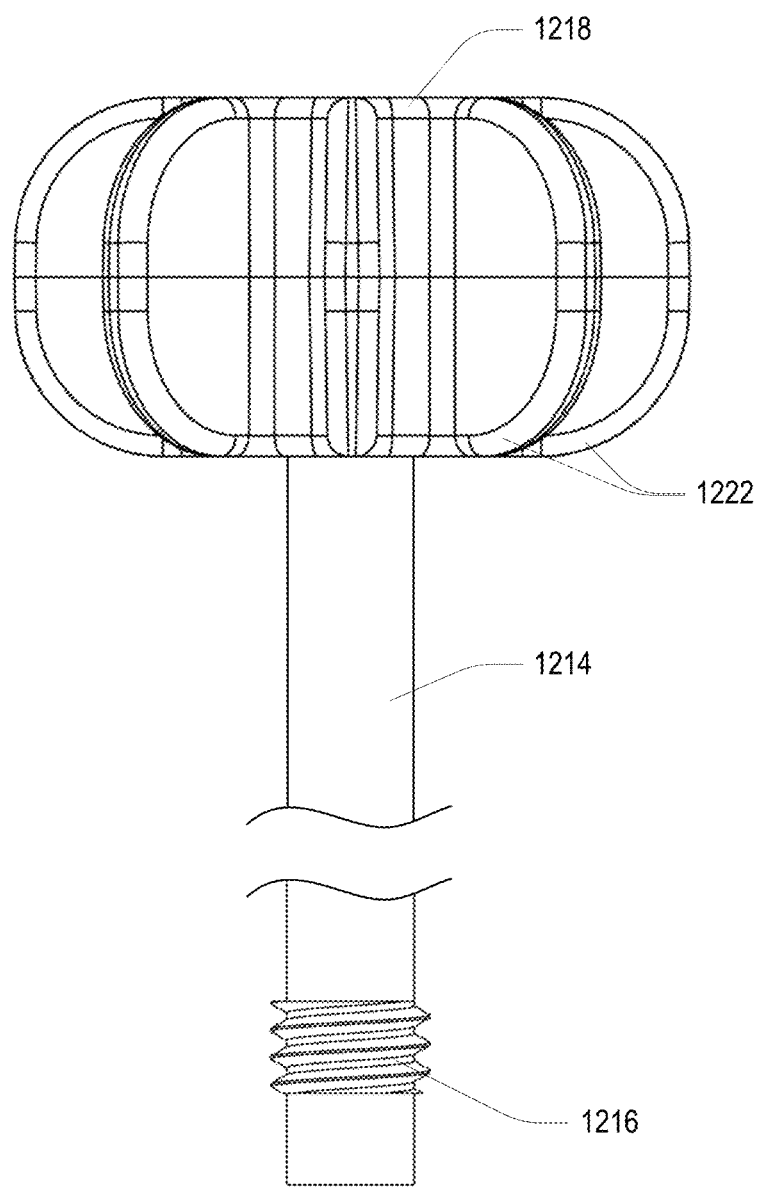
FIG. 12B depicts a front view of a handle knob and internal shaft of the cannulated screwdriver of FIG. 12A.

FIG. 12B depicts the handle knob 1218 attached to the internal shaft 1214 on an end opposite of the threaded portion 1216. The threaded portion 1216 can be configured to be inserted and screwed into a pedicle screw, thereby forming an attachment between the internal shaft and the pedicle screw. Such an attachment can function to prevent the pedicle screw from detaching from the pedicle screw coupling 1204, and can be controlled via the handle knob 1218. As shown, the handle knob 1218 can be a circular body having a flat top surface, a flat bottom surface, and a circular side wall. The circular side wall can include a plurality of ridges 1222 arranged in an axial direction relative to the cannulated tubular body 1202. The handle knob can have a central aperture configured to provide access from the top surface to the bottom surface.

The delivery wire 1250 can be pre-inserted into a surgical site through the cannulation 1208 of the cannulated screwdriver 1200, and thereby allow for the controlled, accurate delivery of a pedicle screw. The pedicle screw coupling can include a cutting element, the cutting element configured to provide access to a surgical site. Once a pedicle screw has been inserted into a surgical site, the delivery wire 1250 can be removed, and the cannulation 1208 can provide access to the lumen of the pedicle screw through the handle 1206, the aperture of the handle knob 1218, and the internal shaft 1214. The cannulated screwdriver 1200 can include a locking mechanism configured to lock the cannulated screwdriver 1200 at a position along the length of the delivery wire 1250. Such a locking mechanism can be incorporated into the handle 1206, and can be configured to contact the delivery wire 1250 within the cannulation 1208, thereby securing the delivery wire 1250.

Figure 13:
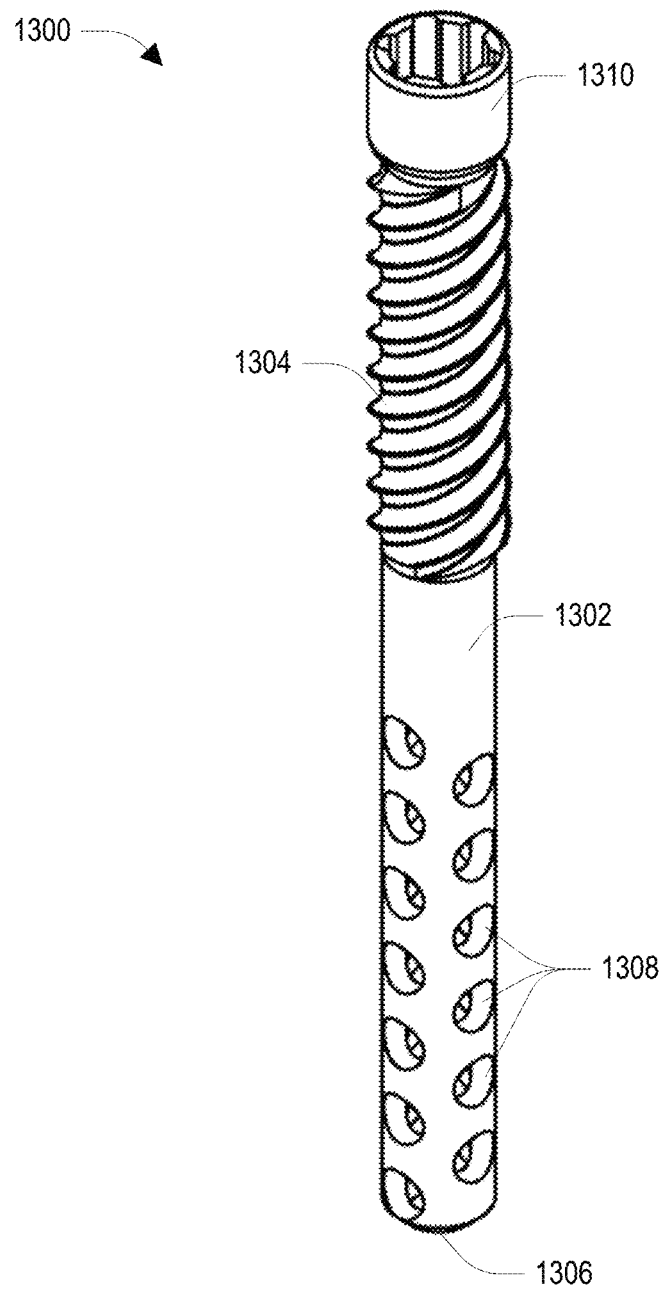
FIG. 13 depicts an isometric view of a pedicle screw.

FIG. 13 depicts an exemplary pedicle screw 1300, which can be utilized in the systems and methods described herein. The depicted pedicle screw 1300 includes a cylindrical body 1302 with threads 1304 positioned thereon. Although threads are depicted, alternative fixation means such as expansion or curved path fixation can be used. A cannulation 1306 can be fluidly connected to several fenestrations 1308 as well as a drill coupling member 1310 through the interior of the cylindrical body 1302. The cannulation 1306 can have a similar size to an associated delivery wire, and thereby allow for delivery of bone cement primarily through the fenestrations 1308. The drill coupling member 1310 can be configured to engage with and be driven by a screw coupling member of a drill. The drill coupling member 1310 can be configured to engage with a rod or comparable connecter attached to a second pedicle screw positioned within the surgical site or within a second surgical site of a different vertebral body. The pedicle screw 1300 can be formed of a rigid, biocompatible material, such as titanium. The pedicle screw 1300 can have a diameter of between about 3 millimeters and about 7 millimeters and/or an axial length of between about 30 millimeters and about 60 millimeters. Multiple pedicle screws can be formed in several different lengths or diameters, and the methods described herein can further involve selecting a pedicle screw having an appropriate length and diameter for a particular surgical site.

Figure 14:
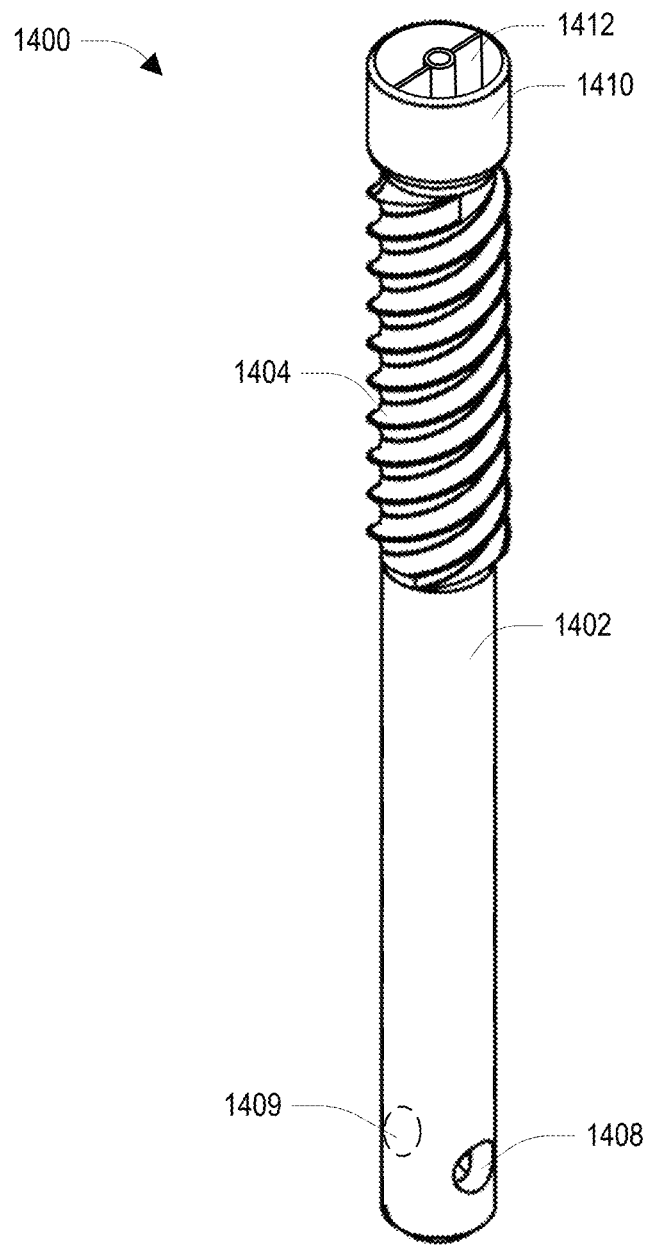
FIG. 14 depicts an isometric view of a pedicle screw.

Although the depicted pedicle screw 1300 has numerous uniformly positioned fenestrations, it should be readily appreciated that fewer fenestrations can be included in alternative arrangements (such as in FIG. 14). For instance, the pedicle screw could have only one fenestration positioned on one part of the cylindrical body 1302. Alternatively, similar to the depicted form, the pedicle screw can comprise a plurality of fenestrations positioned along the axial direction of the pedicle screw in a manner that provides a substantially uniform radial distribution of bone cement.

In one aspect, the pedicle screw 1300 can comprise an expandable balloon covering at least one of the fenestrations, wherein the expandable balloon expands when bone cement exits the at least one fenestration. With the inclusion of the balloon on the pedicle screw itself, the expandable balloon need not be removed from the surgical site. So that the expandable balloon can remain within the surgical site permanently, the balloon can be formed of a biocompatible or a biodegradable material. The expandable balloon can be connected to the pedicle screw through one or more O-ring seals.

In another aspect, the non-threaded portion of the pedicle screw can be configured to rotate relative to the threaded portion. In this manner, by forming the pedicle screw from two rotating bodies, the threaded portion of the pedicle screw can be threaded into bone and remain fixed while the non-threaded portion of the pedicle screw is rotated to control the delivery of bone cement through one or more fenestrations, which can be arranged in a substantially similar axial direction.

FIG. 14 depicts an exemplary pedicle screw 1400, which can be utilized in the systems and methods described herein. The depicted pedicle screw 1400 can include a cylindrical body 1402 with threads 1404 positioned thereon. The threads 1404 can be positioned along only a portion of the cylindrical body 1402, or along the entire length of the cylindrical body 1402. An internal divider 1412 within a drill coupling member 1410 can fluidly separate a first internal chamber comprising a first fenestration 1408 and a second internal chamber comprising a second fenestration 1409. In this manner, the internal divider 1412 can be configured to ensure bone cement introduced into the first chamber only exits out of the first fenestration 1408 and bone cement introduced into the second chamber only exits out of the second fenestration 1409. The first fenestration and the second fenestration can be positioned at the same axial position on opposite sides of the cylindrical body. As shown, the internal divider 1412 can include an internal cannulation that is configured to receive a wire passing through the pedicle screw. The internal cannulation can be fluidly separated from the first chamber and the second chamber.

Figure 15:
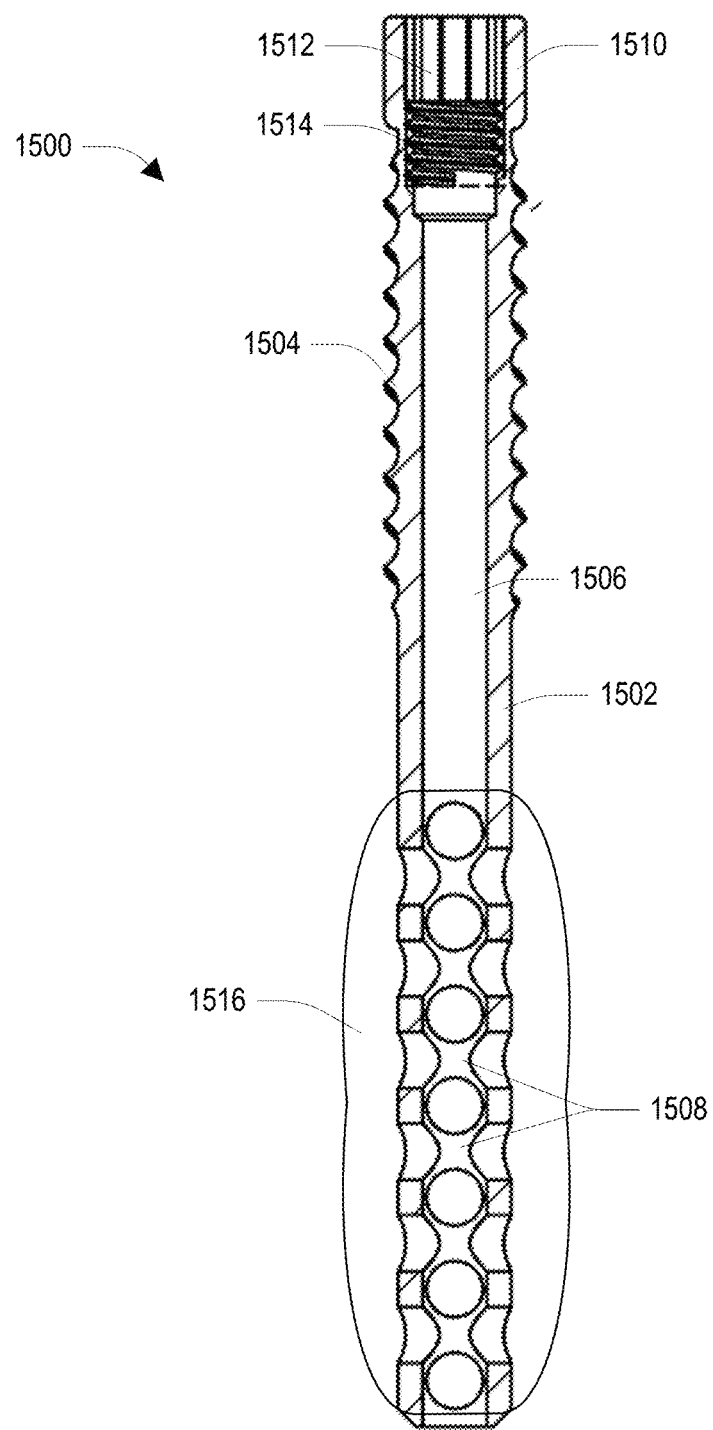
FIG. 15 depicts a front view of a pedicle screw and its internal construction.

FIG. 15 depicts yet another exemplary pedicle screw 1500, which can be utilized in the systems and methods described herein. The depicted pedicle screw 1500 can include a cylindrical body 1502 with threads 1504 positioned thereon. A cannulation 1506 can be fluidly connected to several fenestrations 1508 as well as a drill coupling member 1510 through the interior of the cylindrical body 1502. As shown, the drill coupling member 1510 can include a socket 1512, such as a hexalobular socket or another comparable pedicle screw socket. The drill coupling member 1510 can also include internal threads 1514 to provide further attachment support. An expandable balloon 1516 can be attached as part of the pedicle screw 1500 and can cover at least one of the fenestrations 1508. The expandable balloon 1516 can be configured to expand when the bone cement travels through the cannulation 1506 and exits the fenestrations 1508. The expandable balloon 1516 can be connected to the cylindrical body 1504 through one or more O-ring seals, or using comparable attachment techniques. The expandable balloon 1516 can be dissolvable, and can be biocompatible or biodegradable.

Figure 16:
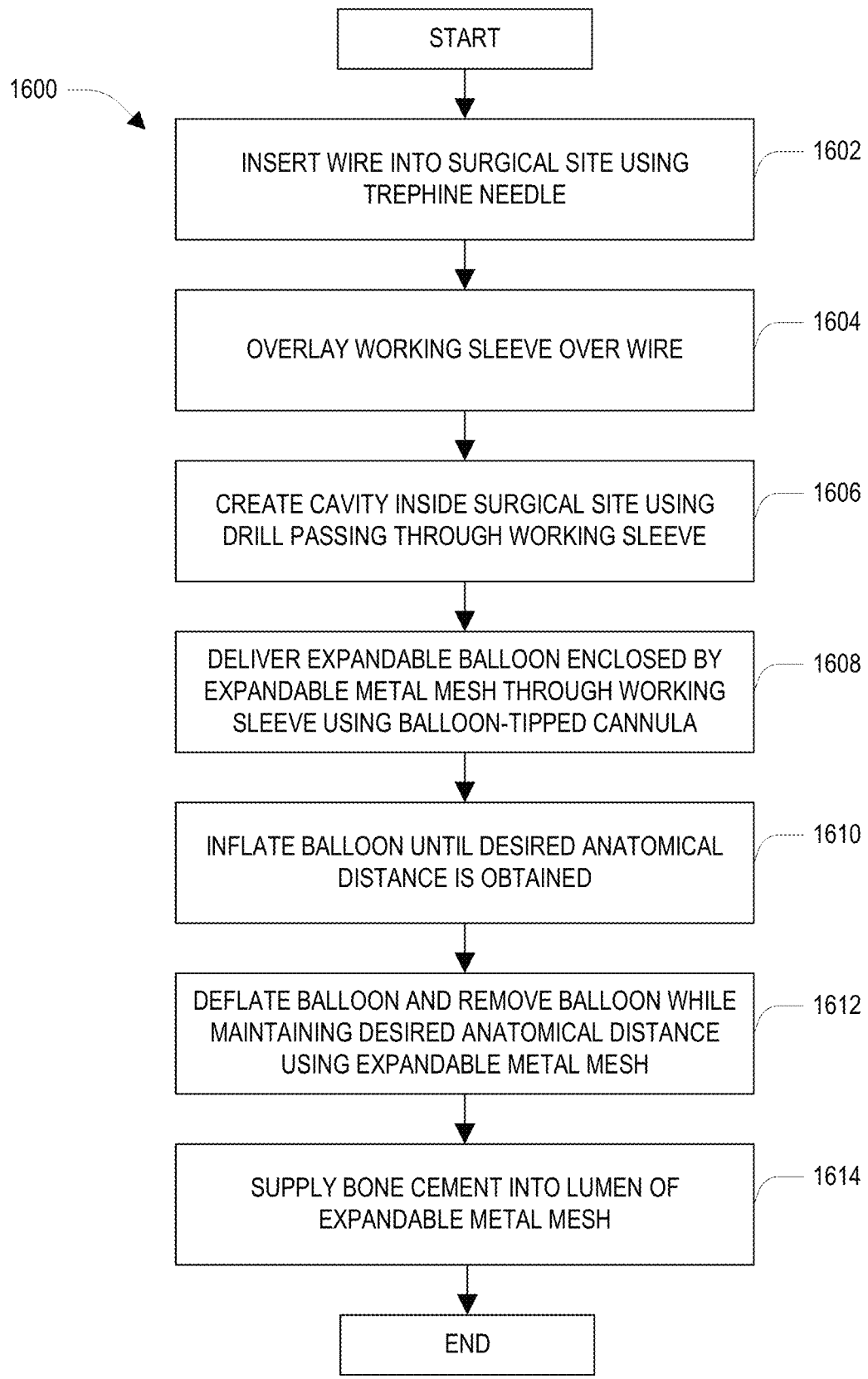
FIG. 16 is a process flow diagram illustrating a spine stabilization procedure.
Figure 17:
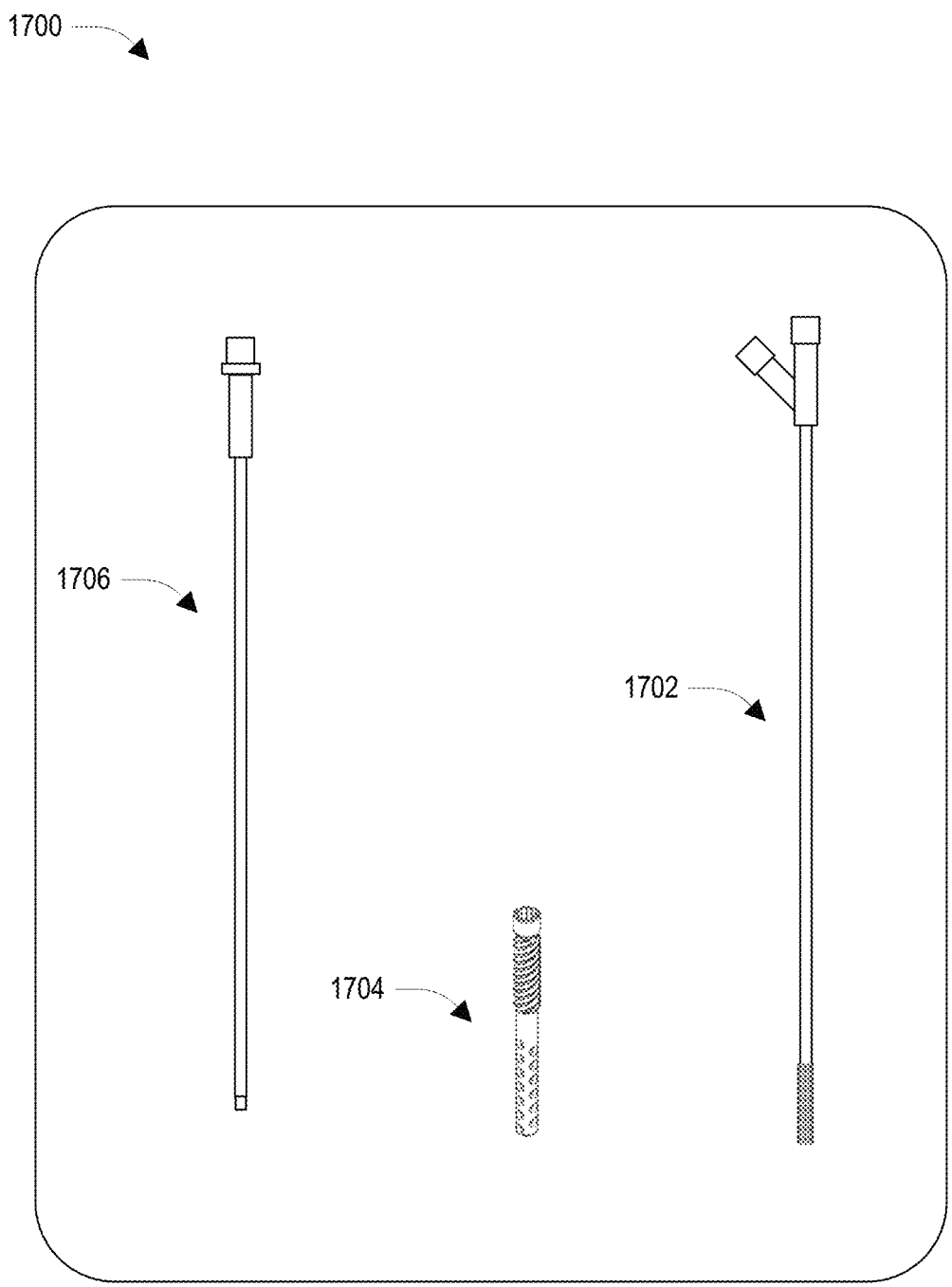
FIG. 17 depicts an exemplary kit for performing a spine stabilization procedure.
Figure 18:
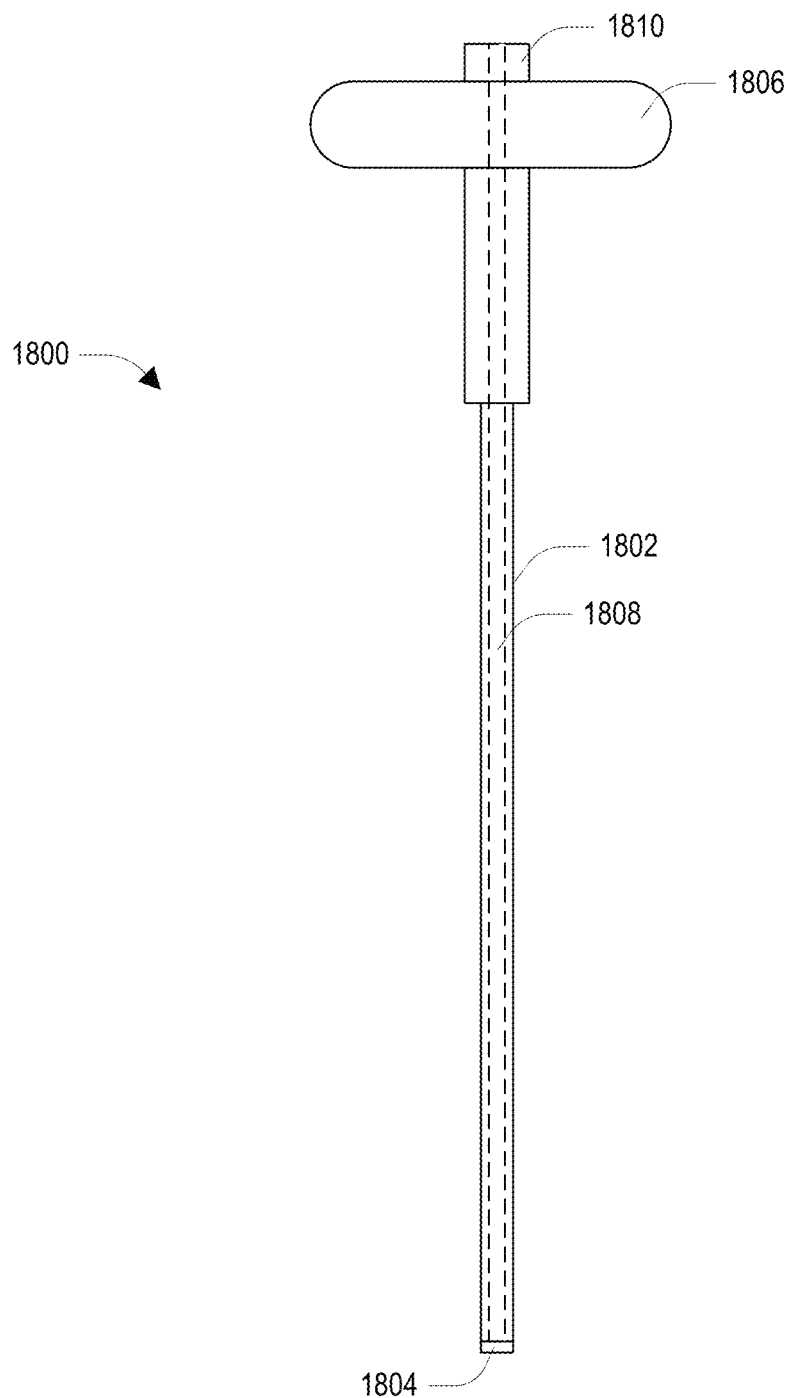
FIG. 18 depicts an exemplary screwdriver system.

FIG. 16 depicts a process flowchart of a spine stabilization procedure 1600, in which, at 1602, a wire can be inserted into a surgical site using a trephine needle having an interlocking hub and stylet. Subsequently, at 1604, a working sleeve can be overlayed over the wire. Next, at 1606, a cavity can be created inside the surgical site. The cavity can be created using a drill passing through the working sleeve. Subsequently, at 1608, an expandable balloon enclosed by an expandable metal mesh can be delivered into the cavity through the working sleeve using a balloon-tipped cannula. Next, at 1610, the balloon can be inflated until a desired anatomical distance is obtained. Subsequently, at 1612, the balloon can be deflated and removed while maintaining the desired anatomical distance using an expandable metal mesh. Next, at 1614, bone cement can be supplied into a lumen of the expandable metal mesh. In this manner, the spine stabilization procedure 1600 can provide stabilization and create the desired anatomical distance in a surgical site without utilizing a pedicle screw. The spine stabilization procedure 1600 can incorporate the teachings described herein, including those detailed for spine stabilization procedure 100 and spine stabilization procedure 200.

FIG. 1700 depicts an exemplary kit for performing a spine stabilization procedure. The kit 1700 can include a balloon-tipped cannula 1702 having an expandable balloon enclosed by an expandable metal mesh, the balloon-tipped cannula configured to pass through a working sleeve and to expand the expandable balloon and expandable metal mesh within a surgical site. The kit 1700 can additionally include a pedicle screw 1704 configured to be inserted into the surgical site and an injection system 1706 configured to supply bone cement to the surgical site through of at least one fenestration or cannulation of the pedicle screw when the pedicle screw is positioned within the injection site. The components of the kit 1700 can be sterile and intended for single use.

The kit 1700 can incorporate any of the devices, materials, or components of the systems and methods described herein. For instance, the injection system 1706 can include a bone cement cannula configured to be inserted through a cannulated screwdriver. The kit 1700 can further include one or more additional pedicle screws, wherein each pedicle screw has a different axial length. The inclusion of multiple different sized pedicle screws can allow a physician to easily select the pedicle screw best suited to the needs of the particular patient and their unique surgical site. The kit 1700 can include a source of bone cement in order to provide a physician convenient access to a quantity of bone cement typically required for a spinal procedure.

Alternative kit arrangements are possible using the systems and devices described herein. For instance, an access kit can include components associated with accessing the surgical site, such as the trephine needle, the working sleeve and associated drill or reamer, the cement cannula, the cannulated screwdriver, and one or more surgical wires. A balloon kit can include the balloon tipped cannula with the associated metal mesh. A screw kit can include multiple quantities of pedicle screws, with each pedicle screw having a different diameter or length. A cement kit can include a cement mixer and cement components, such as a source of bone cement. Any kits described herein are combinable with one another. For example, a access-screw combination kit can include the elements of the access kit and the screw kit. Likewise, a balloon-screw combination kit can include the elements of the balloon kit and the screw kit.

FIG. 1800 depicts an exemplary screwdriver system 1800 with an integrated bone cement injection system in accordance with the techniques described herein. The screwdriver system 1800 can include a cannulated tubular body 1802. The cannulated tubular body 1802 can have a length and diameter specifically selected to fit into a cavity of surgical site. The screwdriver system 1800 can also include a pedicle screw coupling 1804 attached to a first end of the cannulated tubular body 1802. The pedicle screw coupling 1804 can be configured to couple to a pedicle screw in a manner that the pedicle screw can be driven while the cannulated tubular body 1802 is rotated. In order to properly apply sufficient torque to the driving screw, the screwdriver system can include a handle connected to a second end of the cannulated tubular body. Although a hand-driven handle is depicted, it should be readily appreciated that mechanical drive mechanisms can alternatively be used.

The depicted screwdriver system 1800 can include an injection system attached to the cannulated tubular body 1802, the injection system configured to supply bone cement to a coupled pedicle screw through the cannulation of the cannulated tubular body 1802. The injection system can include a cement cannula 1808 positioned within the cannulation of the cannulated tubular body 1802 and a cement cannula port 1810 connected to the cement cannula 1808. The cement cannula can be connected to the cannulated tubular body in a manner that the screwdriver system 1800 can drive a pedicle screw into a surgical site while the cement cannula 1808 is connected, including an attached cement cannula port 1810. In this manner, the cement cannula 1808 can be configured to remain within the cannulated tubular body while the pedicle screw coupling is rotated. In other words, the cement cannula 1808 can be integral to the screwdriver system 1800 during its usage, which can allow for a more efficient operation by eliminating the need for a physician to exchange tools. Similarly, in order to avoid the usage of additional equipment, the tubular body 1802 can have a cutting element positioned on its first end. The addition of a cutting element, such as a reaming or boring bit can allow the screwdriver system 1800 to multi-functionally form a cavity within a surgical site, to insert a pedicle screw, and/or to provide bone cement to the surgical site.

The cement cannula port 1810 can be fluidly connected to the cement cannula, such that bone cement can be introduced through the cement cannula port 1810, pass through the cement cannula 1808, and exit into a pedicle screw coupled to the pedicle screw coupling member 1804. The pedicle screw port 1810 can be configured to fluidly connect the cement cannula 1808 to a syringe, mechanical pump, or similar device capable of providing a pressure differential to introduce bone cement through the screwdriver system 1800. The cement cannula 1808 can include a directional element configured to selectively supply bone cement to a pedicle screw attached to the pedicle screw coupling 1804.

Mechanical Expansion

The present disclosure further provides systems and methods relating to various devices for spinal stabilization procedures that have mechanical expansion components. In other words, in place of utilizing a balloon for expansion in a surgical site as previously described herein, the mechanical expansion devices can additionally or alternatively use mechanical elements to provide a similar expansion force to the surgical site, for instance by using several mechanical supports (e.g., bendable rods or shafts) that expand outward from the device into the surgical site. It should be readily appreciated that such mechanical expansion devices can rely on any of the prior aspects described herein.

Figure 19A:
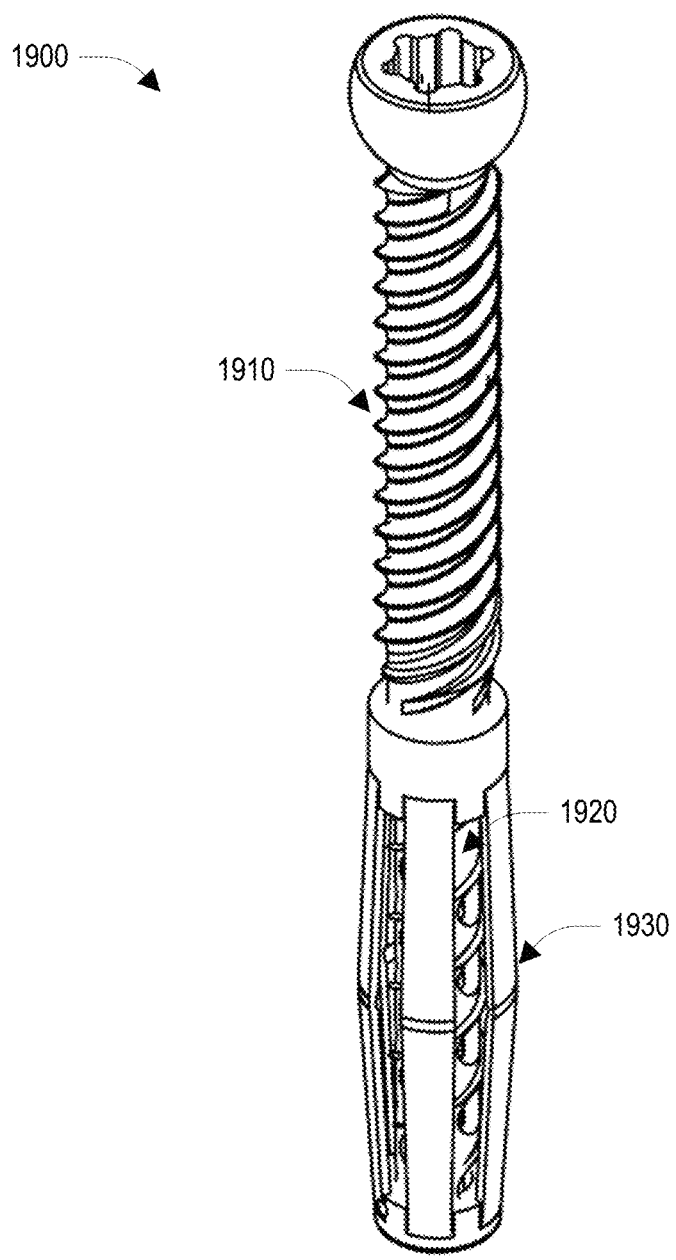
FIG. 19A depicts an isometric view of a pedicle screw with a mechanical expansion component in a collapsed state.
Figure 19B:
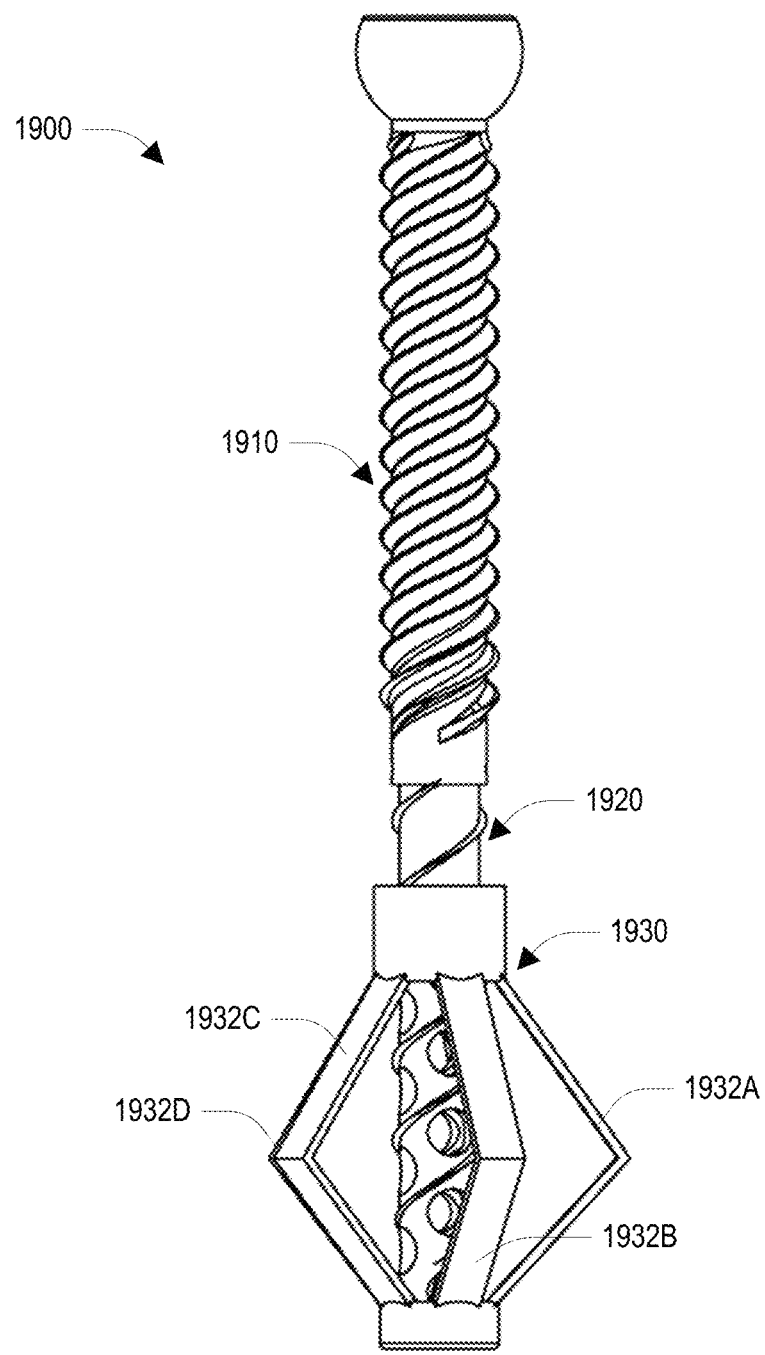
FIG. 19B depicts an isometric view of the pedicle screw of FIG. 19A in an expanded state.

FIGS. 19A-E depict an example a pedicle screw 1900 with a mechanical expansion component 1930 that can be controllably switched from a collapsed state (FIG. 19A) to an expanded state (FIG. 19B). As can be seen in FIG. 19A, the pedicle screw 1900 can be formed of three components, a cannulated tubular body 1920, a threaded cover 1910 which can be coupled to and positioned over one end of the cannulated tubular body 1920, and an expansion component 1930 coupled to the cannulated tubular body. In this example, the cannulated tubular body 1920 can be configured to freely spin within the expansion component 1930, and through this rotating motion, thereby cause the expansion component 1930 to change from a collapsed state to an expanded state, or vice versa. In this manner, the pedicle screw 1900 can be inserted into a surgical site while in collapsed state, at which point an operator can intentionally rotate the cannulated tubular body 1920, thereby expanding the volume of the surgical site. Once the surgical site has been expanded, bone cement can then be injected through the pedicle screw 1900 into the surgical site.

In FIG. 19B, the expansion component 1930 is shown in an expanded state, with four mechanical supports 1932A, 1932B, 1932C, 1932D having undergone a shape change from a substantially linear form to a bent form, thereby protruding in a radial direction from the cannulated tubular body 1920. As shown, compared to FIG. 19A, the expansion component 1930 has shifted downward toward a first end of the pedicle screw 1900 in order to allow for these shape changes in the mechanical supports 1932A, 1932B, 1932C, 1932D. While in this example there are four mechanical supports in the form of bars with center joints that are configured to bend, it should readily be appreciated that an alternative number of mechanical supports having different forms can be utilized.

Figure 19C:
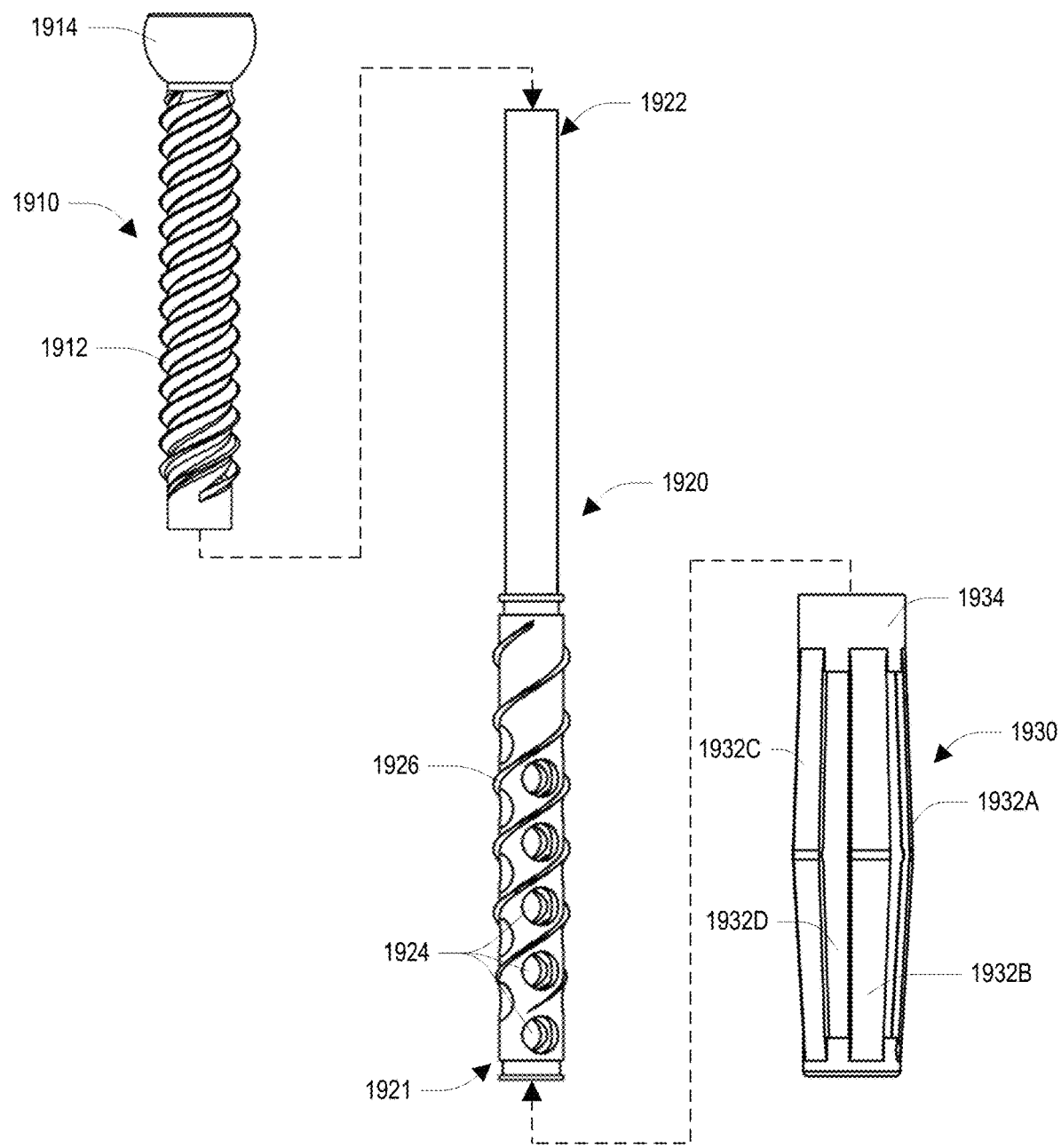
FIG. 19C depicts an exploded view of the pedicle screw of FIGS. 19A-B.
Figure 19D:
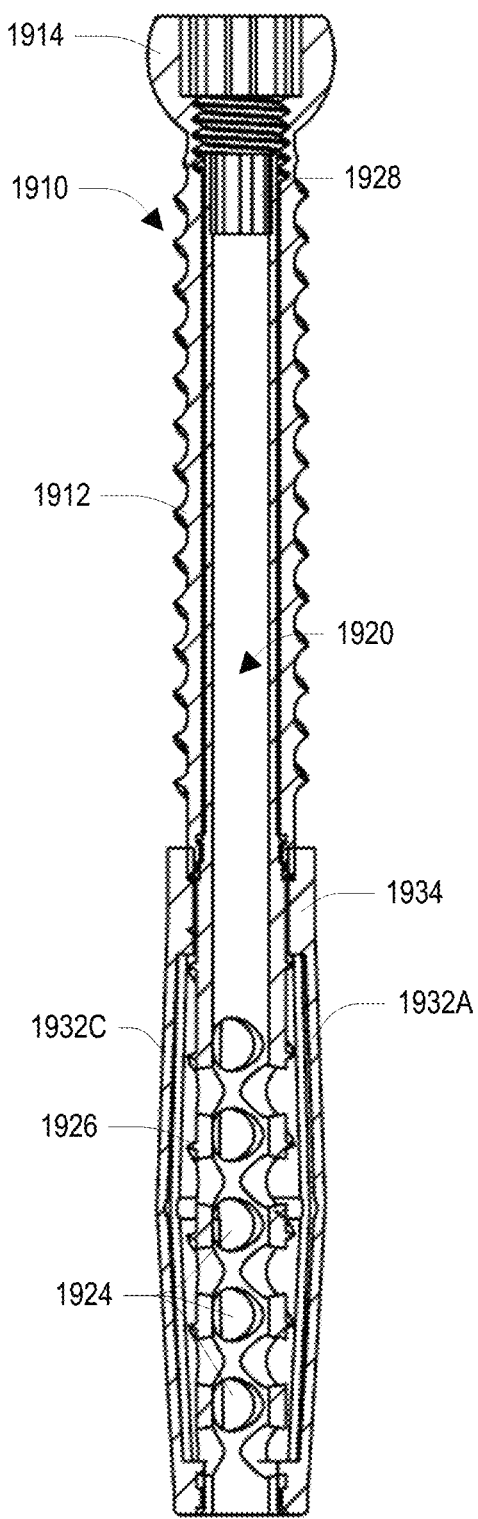
FIG. 19D depicts a front, sectional view of the pedicle screw of FIGS. 19A-C.
Figure 19E:
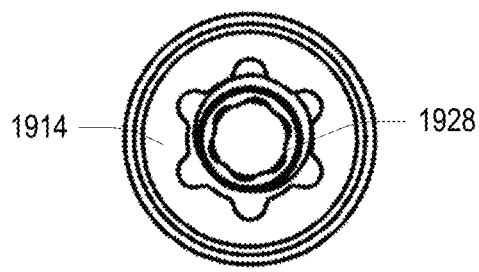
FIG. 19E depicts a top view of the pedicle screw of FIGS. 19A-D.

FIG. 19C depicts an exploded view of the pedicle screw. As depicted, the cannulated tubular body can have a first end 1921 that receives the expansion component 1930, and a second end 1922 that receives the threaded cover 1910. The threaded cover 1910 can include a threaded portion 1912 and a drill coupling member 1914. Although not depicted, the drill coupling member 1914 can include a screw tulip. The expansion component 1930 can include an adjustment element 1934 contacting the mechanical supports 1932A, 1932B, 1932C, 1932D. The adjustment element 1934 can be configured to move in an axial direction along the tubular body 1920, and this movement can shift the mechanical supports 1932A, 1932B, 1932C, 1932D from the collapsed state to the expanded state, or vice versa.

In this example, the cannulated tubular body 1920 includes a plurality of fenestrations 1924, which can aid in the injection of bone cement through the pedicle screw 1900. The cannulated tubular body 1920 can also include an external threaded portion 1926 at the first end 1921. The adjustment element 1934 of the expansion component 1930 can include an internal threaded portion or other structural features configured to contact and interact with external threaded portion 1926 of the tubular body 1920. Based on this interaction, rotation of the cannulated tubular body 1920 can produce axial movement of the adjustment element 1934. As shown, in FIGS. 19D-E, the cannulated tubular body 1920 can include a coupling member 1928 at its second end 1922. The coupling member 1926 can be configured to receive and couple to a driver, thereby allowing an operator to rotate the cannulated tubular body 1920 and controllably modify the state of the expansion component 1930.

The pedicle screw 1900 can further include a handle or related device configured to control the placement of the pedicle screw 1900 and the adjustment of the expansion component 1930. The driver can be configured to couple to the coupling member 1926 and to drive the pedicle screw 1900 into a surgical site. For instance, the driver can include a first handle element (e.g., an outer handle) configured to control the rotation of the threaded cover 1910. To control the expansion component 1930, the driver can further include a second handle element (e.g., an inner handle) configured to rotate to adjust the expansion component 1930. For instance, the first handle element can be held in a stationary position while the second handle element is intentionally rotated, which can produce a rotation in the cannulated tubular body 1920, thereby controllably modifying the state of the expansion component 1930. The driver can specifically be cannulated, such that a cement cannula could be inserted after the surgical site has been expanded. A k-wire can specifically be used to control such a cannulated driver and any subsequent or simultaneous insertion of a cement cannula.

Figure 20A:
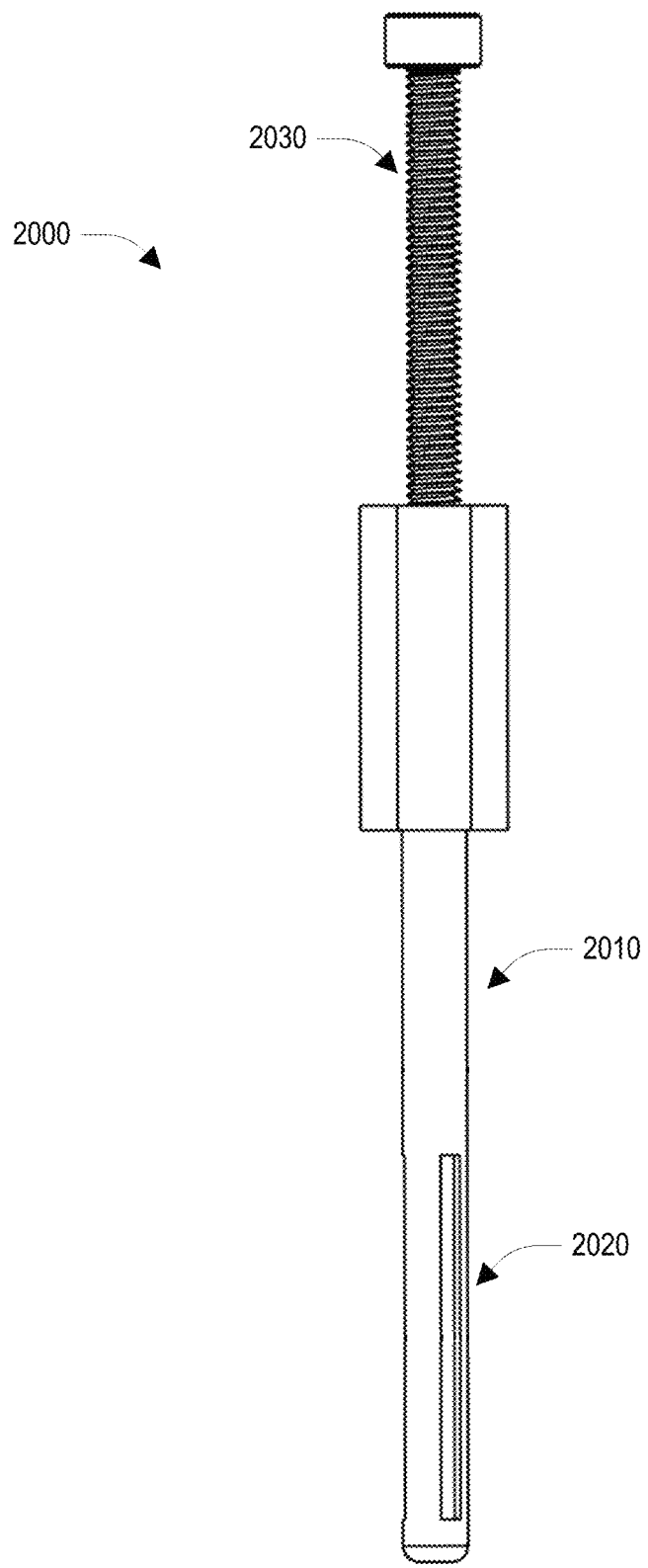
FIG. 20A depicts a front view of a device with a mechanical expansion component in a collapsed state.
Figure 20B:
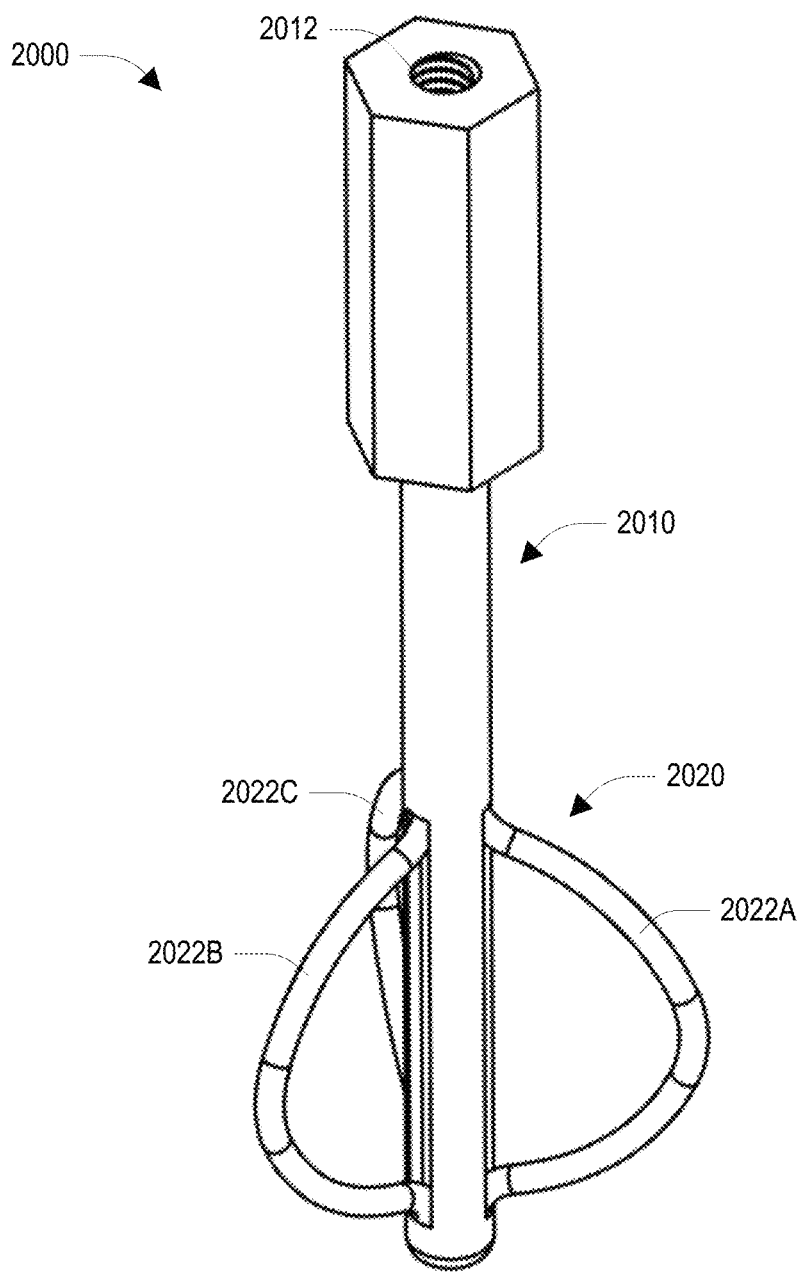
FIG. 20B depicts an isometric view of the device of FIG. 20A in an expanded state.
Figure 20C:
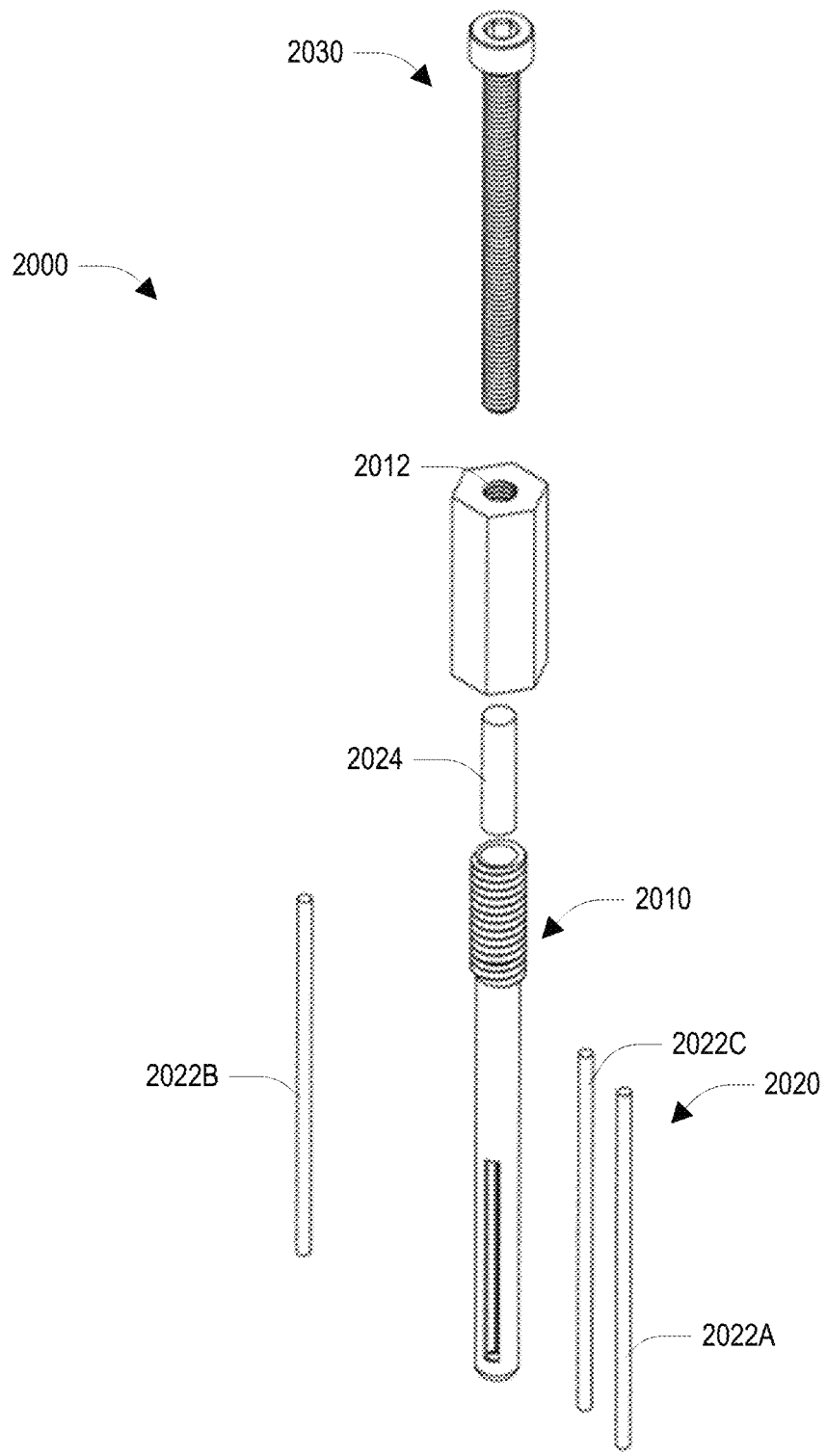
FIG. 20C depicts an exploded view of the device of FIGS. 20A-B.

FIG. 20A depict an expander device 2000 with a mechanical expansion component 2020 that can be controllably switched from a collapsed state (FIG. 20A) to an expanded state (FIG. 20B). As can be seen, the expander device 2000 can generally include a tubular body 2010 configured to be inserted into a spinal surgical site and an expansion component 2020 coupled to the tubular body 2010. The expansion component 2020 can function in a similar manner to the expansion component 1930 of FIGS. 19A-E, switching from a collapsed state to an expanded state in order to provide an expansion force in a surgical site.

In FIG. 20B, the expansion component 2020 is shown in an expanded state, with three mechanical supports 2022A, 2022B, 2022C, having undergone a shape change to arch and bend outward in an radial direction from the tubular body 2010. Unlike the mechanical supports in FIGS. 19A-19B, the mechanical supports 2022A, 2022B, 2022C do not have a designated joint at which to undergo the shape deformation. Rather, the mechanical supports 2022A, 2022B, 2022C can be formed of a elastic material that is configured to bend throughout its length to create the radial expansion. In other words, the mechanical supports 2022A, 2022B, 2022C can be formed of flexible rods that are configured to undergo a change in shape when in the expanded state. While there can be many suitable materials, the mechanical supports 2022A, 2022B, 2022C can specifically comprise or consist essentially of nitinol.

Figure 20D:
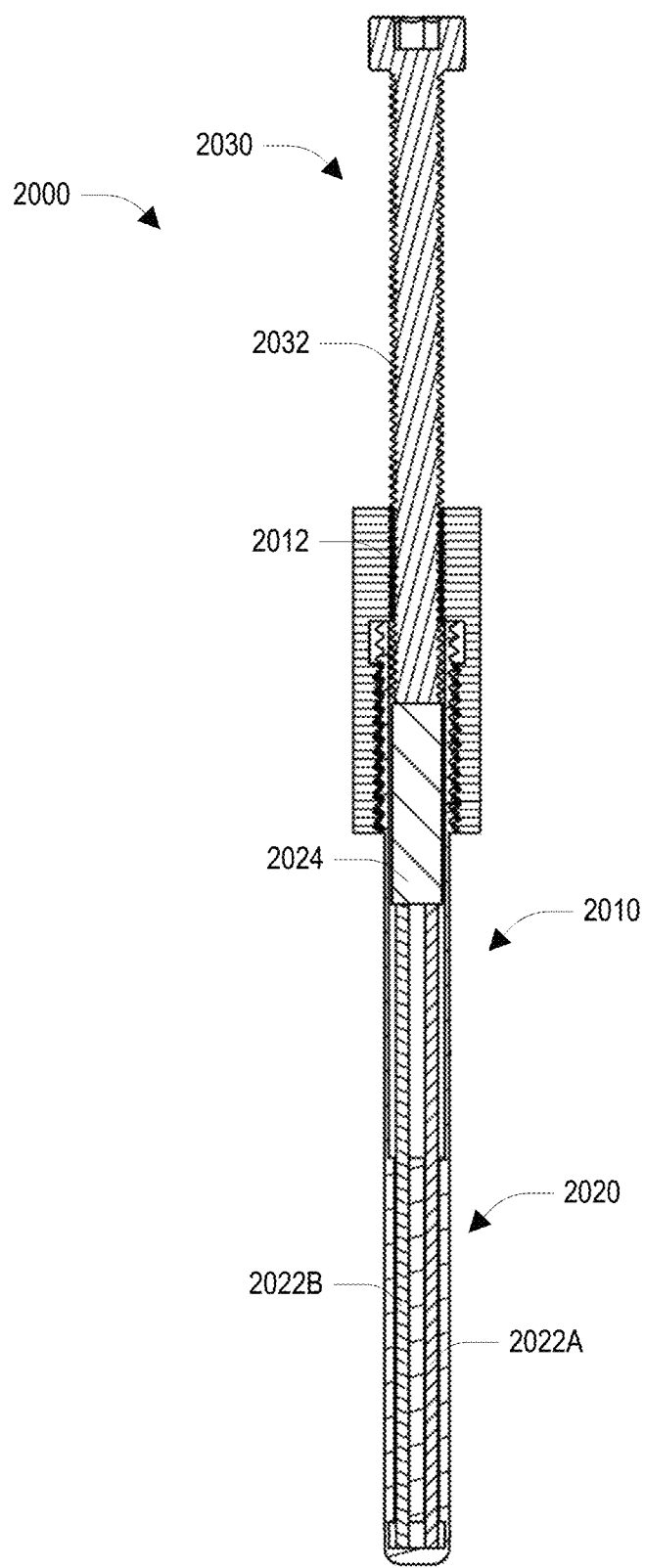
FIG. 20D depicts a front, sectional view of the device of FIGS. 20A-C.

FIG. 20D depicts a sectional view of the expansion device 2000. In this example, a plug 2024 can function as an adjustment element and be positioned within the cannulated tubular body 2010. The plug 2024 can be configured to move in an axial direction and to contact and apply a force to the mechanical supports 2022A, 2022B, 2022C. As shown, the cannulated tubular body 2010 can include an internal threaded portion 2012, which can be axially adjacent to the plug when the mechanical supports are in a collapsed state. A bolt 2030 with threads 2032, or a similar threaded component, can be rotated to apply a downward force on the plug 2024, thereby moving the plug 2024 in an axial direction and changing the state of the expansion component 2020.

The expansion device 2000 can further include a handle or related device configured to control the placement of the expansion device 2000 and the adjustment of the expansion component 2020. For example, a first handle element (e.g., an outer handle) can be coupled to the tubular body 2010 and a second handle element can be coupled to the expansion component 2020, for instance, by either directly or indirectly contacting the plug 2024. The second handle element can be configured so that a rotation of the second handle element produces axial movement of the plug 2024 and thereby adjusts the state of the expansion component 2020. When adjusting the state of the expansion component 2020 using the second handle element, the first handle element can be held in a stationary position to prevent movement of the rest of the expansion device 2000.

Although not depicted in these examples, but consistent with the above description, a mesh or similar structure can be positioned adjacent to the mechanical supports 2022A, 2022B, 2022C and configured to expand in a radial direction along with the mechanical supports 2022A, 2022B, 2022C. The use of such a mesh can help to ensure that the surgical site is adequately and uniformly expanded, and to ensure the controlled injection of any subsequently-injected bone cement.

Although many of the devices and systems described herein are discussed as manual powered tools, which can provide improved control and accuracy during a procedure, it should be readily appreciated that machine powered tools and techniques can be substituted therefor.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. Other implementations can be within the scope of the following claims.

What is claimed is:

1. A device for a spinal stabilization procedure comprising:
  a cannulated tubular body having an end configured to be inserted into a surgical site; and
  an expansion component coupled to the cannulated tubular body comprising:
    a plurality of elongated mechanical supports configured to (i) be axially aligned with the cannulated tubular body when in a collapsed state, and (ii) bend outward in a radial direction when in an expanded state; and
    an adjustment element contacting the mechanical supports which is configured to move in an axial direction such that movement of the adjustment element toward the end of the cannulated tubular body shifts the mechanical supports from the collapsed state to the expanded state,
    wherein a portion of the adjustment element is threaded and the cannulated tubular body is configured to rotate within the adjustment element in order to move the adjustment element in the axial direction.

2. The device of claim 1, wherein at least a portion of the mechanical supports comprise a bar with a center joint, at least a portion of the mechanical supports being configured to bend at the center joints when in the expanded state.

3. The device of claim 1, wherein the mechanical supports are formed of flexible rods configured to undergo a change in shape when in the expanded state.

4. The device of claim 1, further comprising a handle including:
  a first handle element coupled to the cannulated tubular body; and
  a second handle element coupled to the expansion component, wherein rotation of the second handle element produces the movement of the adjustment element.

5. The device of claim 1, further comprising:
  a mesh positioned adjacent to the mechanical supports;
  wherein the mechanical supports are configured to contact and expand the mesh in the expanded state.

6. The device of claim 1, further comprising a threaded portion configured to be secured to a bone within the surgical site.

7. A pedicle screw for use in a spine stabilization procedure comprising:
  a cannulated tubular body having a first end configured to be inserted into a surgical site and a second end;
  a threaded cover positioned over the second end of the cannulated tubular body, the threaded cover configured to be secured to a bone within a surgical site; and
  an expansion component coupled to the cannulated tubular body comprising:
    a plurality of elongated mechanical supports configured to (i) be axially aligned with the cannulated tubular body when in a collapsed state, and (ii) bend outward in a radial direction when in an expanded state;
    an adjustment element contacting the mechanical supports which is configured to move in an axial direction such that movement of the adjustment element toward the first end of the cannulated tubular body shifts the mechanical supports from the collapsed state to the expanded state,
    wherein a portion of the adjustment element is threaded and the cannulated tubular body is configured to rotate within the adjustment element in order to move the adjustment element in the axial direction.

8. The pedicle screw of claim 7, wherein the cannulated tubular body is configured to freely rotate within the threaded cover.

9. The pedicle screw of claim 7, wherein the cannulated tubular body comprises an external threaded portion at the first end.

10. The pedicle screw of claim 7, wherein the mechanical supports comprise a bar with a center joint, at least a portion of the mechanical supports being configured to bend at the center joints when in the expanded state.

11. The pedicle screw of claim 7, wherein the cannulated tubular body further comprises a fenestration positioned along cannulated tubular body.

12. The pedicle screw of claim 7, wherein threaded cover further comprises a drill coupling member.

13. The pedicle screw of claim 12, wherein the drill coupling member comprises a screw tulip.

14. A device for a spinal stabilization procedure comprising:
  a cannulated tubular body having an end configured to be inserted into a surgical site; and
  an expansion component coupled to the cannulated tubular body comprising:
    a plurality of elongated mechanical supports configured to (i) be axially aligned with the cannulated tubular body when in a collapsed state, and (ii) bend outward in a radial direction when in an expanded state; and
    an adjustment element contacting the mechanical supports which is configured to move in an axial direction such that movement of the adjustment element toward the end of the cannulated tubular body shifts the mechanical supports from the collapsed state to the expanded state;
  a first handle element coupled to the cannulated tubular body; and
  a second handle element coupled to the expansion component, wherein rotation of the second handle element produces the movement of the adjustment element.

15. The device of claim 14, wherein at least a portion of the mechanical supports comprise a bar with a center joint, at least a portion of the mechanical supports being configured to bend at the center joints when in the expanded state.

16. The device of claim 14, wherein the mechanical supports are formed of flexible rods configured to undergo a change in shape when in the expanded state.

17. The device of claim 14, further comprising:
a mesh positioned adjacent to the mechanical supports;
wherein the mechanical supports are configured to contact and expand the mesh in the expanded state.

18. The device of claim 14, further comprising a threaded portion configured to be secured to a bone within the surgical site.

19. The device of claim 14, wherein the cannulated tubular body further comprises a fenestration positioned along the cannulated tubular body.

20. The device of claim 14, further comprising a threaded cover positioned over the second end of the cannulated tubular body, the threaded cover configured to be secured to a bone within a surgical site.

21. The device of claim 20, wherein the threaded cover further comprises a drill coupling member.

22. The device of claim 21, wherein the drill coupling member comprises a screw tulip.

\* \* \* \* \*